(12) United States Patent
Haselton et al.

(10) Patent No.: US 9,575,061 B2
(45) Date of Patent: Feb. 21, 2017

(54) LIQUID DROP DIAGNOSTIC ASSAYS

(75) Inventors: Frederick R. Haselton, Nashville, TN (US); Joshua Robert Trantum, Nashville, TN (US); David W. Wright, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 711 days.

(21) Appl. No.: 13/502,966

(22) PCT Filed: Oct. 20, 2010

(86) PCT No.: PCT/US2010/053387
§ 371 (c)(1),
(2), (4) Date: Jul. 17, 2012

(87) PCT Pub. No.: WO2011/050070
PCT Pub. Date: Apr. 28, 2011

(65) Prior Publication Data
US 2012/0276523 A1    Nov. 1, 2012

Related U.S. Application Data

(60) Provisional application No. 61/253,432, filed on Oct. 20, 2009.

(51) Int. Cl.
*G01N 33/534* (2006.01)
*G01N 33/543* (2006.01)
*G01N 33/569* (2006.01)

(52) U.S. Cl.
CPC .. *G01N 33/54313* (2013.01); *G01N 33/54393* (2013.01); *G01N 33/56905* (2013.01)

(58) Field of Classification Search
CPC ............... G01N 33/54313; G01N 33/54393; G01N 33/56905
USPC ................................................ 436/526, 525
See application file for complete search history.

(56) References Cited

U.S. PATENT DOCUMENTS

| | | | |
|---|---|---|---|
| 5,376,556 A * | 12/1994 | Tarcha et al. | 436/525 |
| 2003/0211488 A1* | 11/2003 | Mirkin et al. | 435/6 |
| 2004/0043512 A1* | 3/2004 | Song et al. | 436/526 |
| 2005/0275837 A1* | 12/2005 | Zhang et al. | 356/301 |
| 2009/0197347 A1 | 8/2009 | Sohn et al. | |

OTHER PUBLICATIONS

Fang et al. "Aggregation and surface-enhanced Raman activity study of dye-coated mixed silver-gold colloids". Journal of Raman Spectroscopy, 2004; 35: 914-920.*

(Continued)

*Primary Examiner* — Mark Shibuya
*Assistant Examiner* — Pensee Do
(74) *Attorney, Agent, or Firm* — Parker Highlander PLLC

(57) ABSTRACT

The present invention provides simple and inexpensive assays for the detection of virtually any analyte in any sample that is in liquid form or that can be solubilized. The assays utilize the fluid dynamics of drop evaporation whereby soluble materials, including analytes and particles binding thereto, are drawn to the edge of the drop and ultimately form a concentrated residual ring. The presence or absence of certain reagents can then be detected through a number of different approaches.

28 Claims, 23 Drawing Sheets

(56) References Cited

OTHER PUBLICATIONS

Ming et al. "Ordered Gold Nanostructure Assemblies Formed by Droplet Evaporation", A Journal of the Gesellschaft Deutscher Chemiker, vol. 47, Issue 50, Dec. 1, 2008 pp. 9680-9690.*
Baker et al., "Genetic Diversity of Plasmodium falciparum Histidine-Rich Protein 2 (PfHRP2) and Its Effect on the Performance of PfHRP2-Based Rapid Diagnostic Tests." *J Infect Dis*, 192, 870-7, 2005.
Deegan et al., "Capillary flow as the cause of ring stains from dried liquid drops." *Nature*, 389, 827-829, 1997.
Kifude et al., "Enzyme-linked immunosorbent assay for detection of Plasmodium falciparum histidine-rich protein 2 in blood, plasma, and serum." *Clin Vaccine Immunol*, 15, 1012-8, 2008.
Martin et al., "Unified parasite lactate dehydrogenase and histidine-rich protein ELISA for quantification of Plasmodium falciparum." *Am J Trop Med Hyg*, 80, 516-22, 2009.
Moody, A., "Rapid diagnostic tests for malaria parasites." *Clin Microbiol Rev*, 15, 66-78, 2002.
Ochola et al., "The reliability of diagnostic techniques in the diagnosis and management of malaria in the absence of a gold standard." *Lancet Infect Dis*, 6, 582-8, 2006.
PCT International Preliminary Report on Patentability issued in International Application No. PCT/US2010/053387, issued Apr. 24, 2012.
PCT International Search Report and Written Opinion issued in International Application No. PCT/US2010/053387, mailed Dec. 23, 2010.
Quintana et al. "Malaria diagnosis by dipstick assay in a Honduran population with coendemic Plasmodium falciparum and Plasmodium vivax.." *S. Am J Trop Med Hyg*, 59, 868-71, 1998.
Singh et al., "Field evaluation of the ICT malaria P.f/P.v immunochromatographic test for diagnosis of Plasmodium falciparum and P.vivax infection in forest villages of Chhindwara, central India." *Trop Med Int Health*, 5, 765-70, 2000.

* cited by examiner

MVSFSKNKVLSAAVFASVLLLDNNNSAFNNNLCSKNAKGLNLNKRLLHETQAHVDDA
HHAHHVADAHHAHHAHHAADAHHAHHAADAHHAHHAADAHHAHHAADAHHAHHAA
DAHHAHHAADAHHAHHAADAHHAHHAADAHHAHHAADAHHAHHAAYAHHAHHASD
AHHAADAHHAAYAHHAHHAADAHHAADAHHAAYAHHAHHAADAHHAADAHHATDAH
HAHHAADAHHATDAHHAADAHHAADAHHATDAHHAADAHHATDAHHAADAHHAADA
HHATDSHHAHHAADAHHAAAHHATDAHHAAAHHATDAHHAAAHHEAATHCLRH

FIG. 10

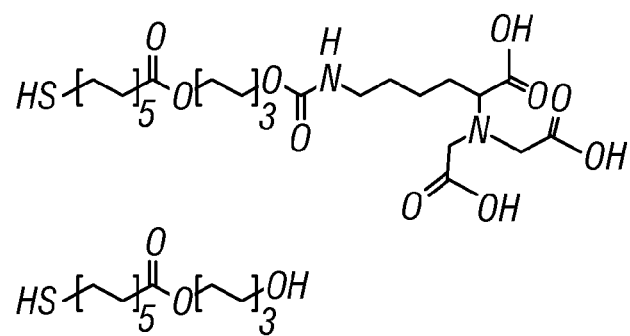

FIG. 11

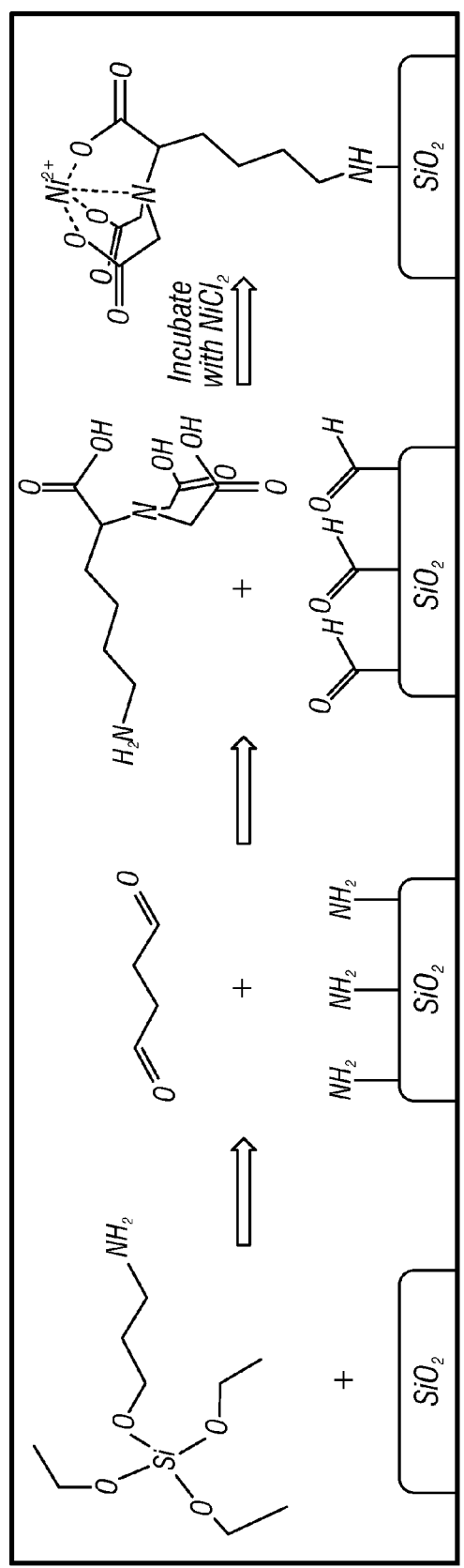
FIG. 17A
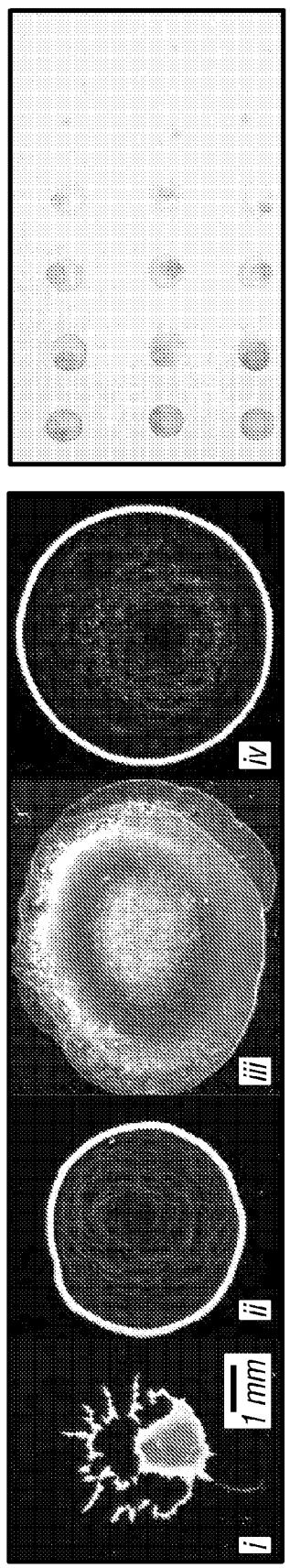
FIG. 17C
FIG. 17B

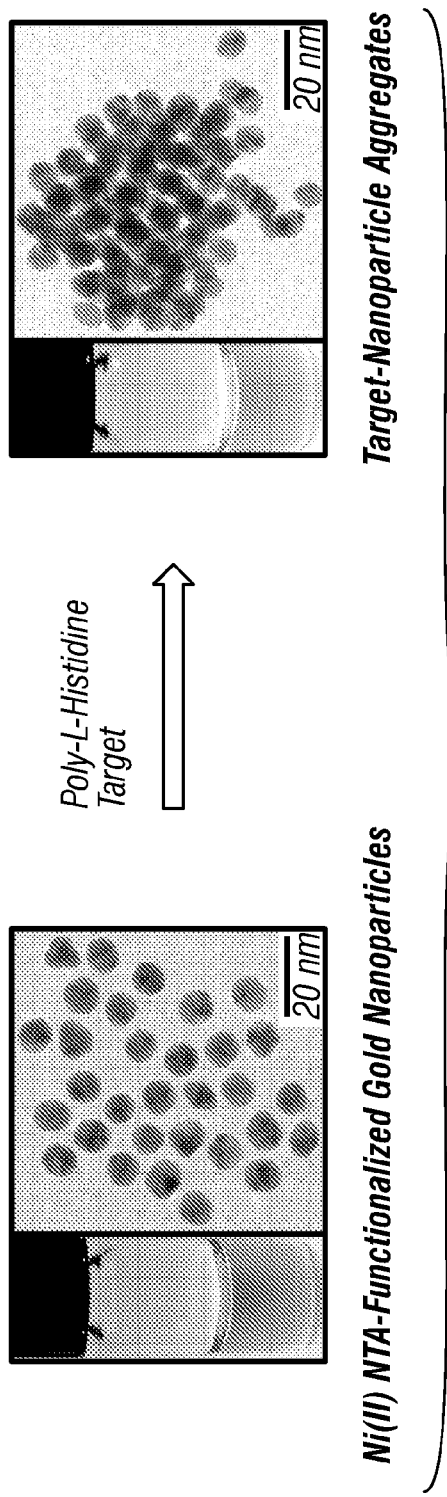
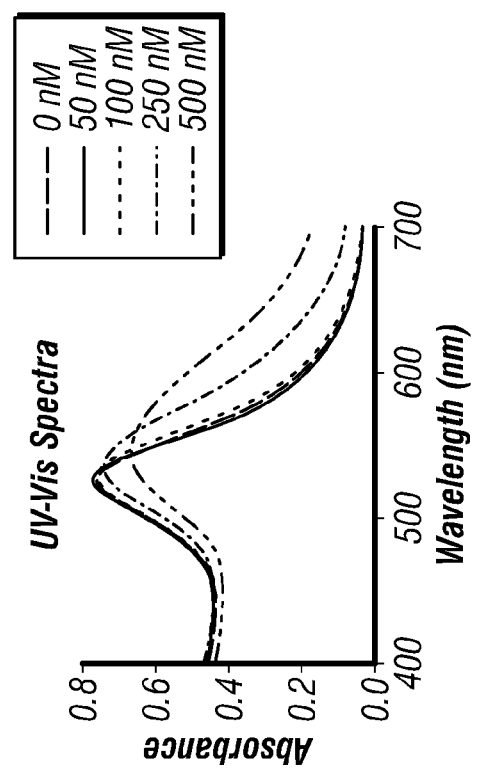
FIG. 18A
FIG. 18B

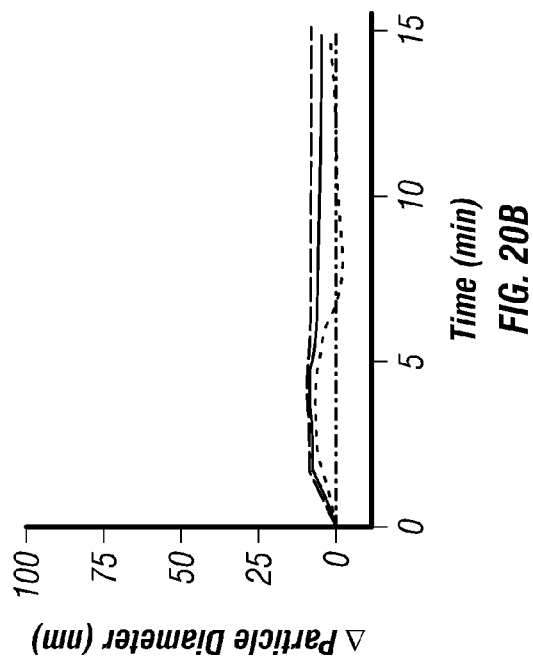
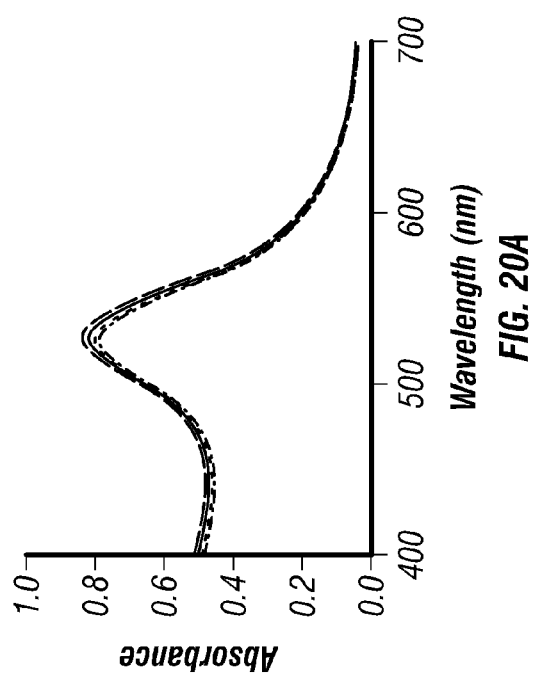
FIG. 20A  FIG. 20B
FIG. 20C  FIG. 20D

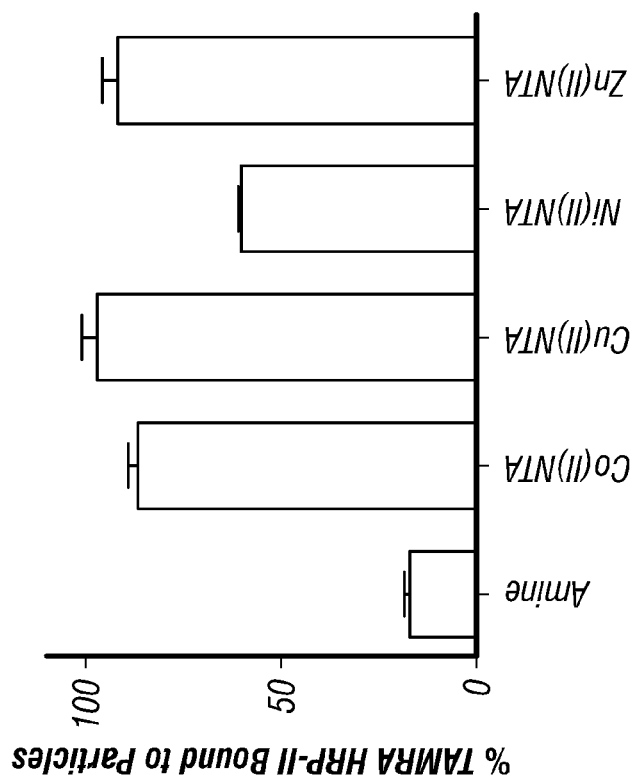
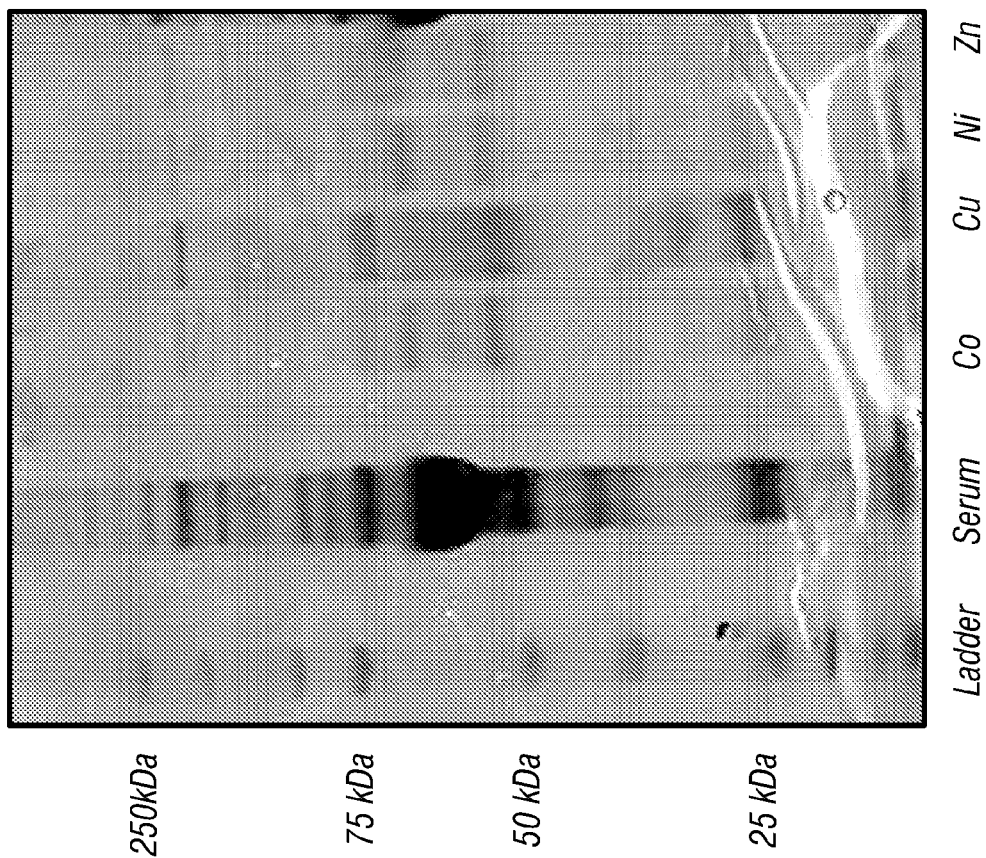
FIG. 22A
FIG. 22B

LIQUID DROP DIAGNOSTIC ASSAYS

This application is a national phase application under 35 U.S.C. §371 of International Patent Application No. PCT/US2010/053387 filed Oct. 20, 2010 which claims benefit of priority to U.S. Provisional Application Ser. No. 61/253,432, filed Oct. 20, 2009, the entire contents of both applications being hereby incorporated by reference.

This invention was made with government support under grant nos. R21EB009235, R21 EY017552, and R21 HL095119, awarded by the National Institutes of Health. The government has certain rights in the invention.

BACKGROUND OF THE INVENTION

I. Field of the Invention

The present invention relates to the fields of biology and diagnostics. More specifically, the invention deals with "drop"-based technologies that permit simple, fast and accurate detection of most any analyte in environmental, plant, medical and other samples.

II. Related Art

A major stumbling block to low resource and/or home diagnostics is simplicity of design. Complex designs drive up the cost of manufacturing and limit distribution. But even clearing this hurdle is no guarantee, since complex designs also fail with improper use by those unskilled in their principles of operation. Thus, a diagnostic design that is inexpensive to manufacture, is simple to operate and can be readily interpreted by the unskilled end-user at home would be highly desirable. The desperate need for such an assay is well-demonstrated by the continuing health management issues surrounding malarial infections, with 250 million cases of malaria being reported in 2006, and having with a mortality rate of 881,000 individuals (FIG. 1) (WHO, 2006)

Traditionally, the "gold standard" for malarial detection has been microscopic examination of thick and/or thin blood films, where an experienced microscopist counts the number of parasites found per unit volume of blood (Warhurst & Williams, 1996). Other methods have also been developed, including fluorescence staining (Gay et al., 1996; Cooke et al., 1992; Srinivasan et al., 2000), amperometric immunosensing (Sharma et al., 2008), and single and multiplexed PCR techniques (Snounou et al., 1993). Recently, a new strategy using an enzyme-linked immunosorbent assay (ELISA) has been reported that detects the presence Histidine-Rich Protein 2 (pfHRP2), which is found specifically in *P. falciparum* induced malarial infection (Kifude et al., 2008; Martin et al., 2009). Although all of these techniques have limits of detection of <100 parasites/μl, they are limited primarily to the laboratory due to their sensitivity to environmental changes, requirements for specialized reagents, slow developing time, and reliance on sophisticated equipment for an interpretable readout. This is problematic since a majority of malarial infections occur in regions where advanced scientific technology and personnel are not readily available. Therefore, diagnostic strategies that are simple to use and require reagents and equipment that are easy to transport and stable in a variety of environmental conditions must be developed.

To circumvent these challenges, rapid diagnostic tests (RDTs) have been developed over the last two decades (Moody, 2002; Quintana et al., 1998; Singh et al., 2000). Although these techniques have performed well in laboratory testing, show high sensitivity, and acceptable limits of detection (<100 parasites/μL), these techniques have not performed well when subjected to variable temperature and humidity conditions due to their reliance on antibodies with small stability ranges (Ochola et al., 2006). In addition, there have been reports that mutations of pfHRP2 found in the Asia-Pacific region reduce the sensitivity of antigen detection due to the antibodies high specificity in the RDTs (Baker et al., 2005). Thus, even further improved and more effective diagnostic assays are needed.

SUMMARY OF THE INVENTION

Thus, in accordance with the present invention, there is provided a method for detecting an analyte in a sample comprising (a) providing a sample in a liquid form; (b) contacting the liquid sample with a capture particle that binds the analyte; (c) placing a drop of the liquid sample on a non-permeable surface, and (d) incubating the surface under conditions promoting evaporation of the drop, wherein the presence or absence of the analyte or capture particle at the droplet edge is detected.

The capture particle may comprise (i) is a latex bead, a polystyrene bead, semi-conductor bead/quantum dot, a metal particle, a paramagnetic particle, or a superparamagnetic particle; and (ii) an analyte binding agent. The analyte binding agent may be a protein, a chemical, a nucleic acid, a metal, or a carbohydrate. The protein analyte binding agent may be an antibody, receptor, an antigen, or a fragment of any of the foregoing. Alternatively, the capture particle may be an isolated antibody or antibody fragment. The capture particle may be 1 nm to 100 μm in diameter, and may be 1.001 gm/cm$^3$ to 5 gm/cm$^3$, or 1.001 gm/cm$^3$ to 20 gm/cm$^3$.

Detection may comprise visual detection with the naked eye, visual detection with a microscope, or automated detection of a light, a fluorescent, a color or a radioactive signal associated with the capture particle. Detection may further comprise quantitation of the signal. The drop may form a spot of between 0.05 μm and 1000 μm, 0.05 μm and 5000 μm. The drop volume may be between 0.1 μl to 100 μl. The capture particle may further comprise an agent that reduces non-specific binding to other reagents. The method may further comprise using a detection particle that forms an aggregate with the capture particle in the presence of the analyte, and a detectable energy transfer reaction between the capture and detection particle occurs in the aggregate.

The non-permeable surface may be a glass, plastic or metal coated slide, a glass, plastic or metal rod, a glass, plastic or metal capillary tube, or a microarray pen. The surface may be flat. The non-permeable surface may be derivatized to bind the capture particle, or to bind the analyte, or to affect contact angle of a fluid. The analyte may be a protein, a nucleic acid, a toxin, a lipid, a carbohydrate, a drug or chemical, or a metal. The protein is a peptide, an antibody (to a pathogen, to a cancer antigen, to an autoantigen), an enzyme, a hormone, a pathogen antigen, a toxin, a cancer antigen, or a fragment of any of the foregoing. The liquid may comprise a solvent selected from water, acetone, methanol, toluene, and ethanol. The sample may be a foodstuff, water, soil, plant material, a biopsy, bronchial lavage, nasal lavage, nasal swab, cheek swab, or a body fluid. The body fluid is urine, spinal fluid, blood, plasma, serum, synovial fluid, mucous, occular fluid, sputum, saliva, or semen.

The method may further comprise washing the non-permeable surface after step (d). The method may also further comprise adding a detection agent that detects (i) the capture particle bound to the analyte at the droplet edge or (ii) analyte at the droplet edge. The capture particle may exhibits a detectable change when aggregated, such as colorimetric, magnetic or spectrometric change. The capture particle may be labeled, such as with an enzyme, a fluorescent label, a chemilluminescent label, a radioactive label, or a colorimetric label. The label may permit amplification.

The mixture of step (b) may be incubated for between 10 seconds, to 10 minutes, to 24 hours prior to step (c). The capture particle may be located on the non-permeable surface, and steps (b) and (c) are comprised in a single step of dropping the sample onto the non-permeable surface. Steps (b) and (c) may be reversed in order.

The method may further comprise use of a control particle that provides a positive control reaction. The method may further comprise use of a precipitating particle that binds to the analyte and prevents movement of the capture particle to the edge of the drop. The method may further comprise use of a precipitating particle that binds to the analyte and prevents movement of the capture particle to the edge of the drop. The precipitating particle is magnetic, and the drop is subjected to a magnetic field, or wherein the precipitating particle is larger and/or heavier than the capture particle, and the drop is subjected to centrifugation.

In another embodiment, there is provided a method for detecting an analyte in a sample comprising (a) providing a sample in a liquid form; (b) contacting the liquid sample with (i) a capture particle that binds the analyte, wherein the capture particle is labeled with a first color, (ii) a control reaction particle labeled with a second color, and (iii) a precipitating particle that binds the analyte; (c) placing a drop of the liquid sample in step (b) on a non-permeable surface; (d) incubating the surface under conditions promoting evaporation of the drop; and (e) detecting the second color at the droplet edge when the analyte is present, or detecting a combination of the first and second colors at the droplet edge when the analyte is not present. The surface may be flat.

The precipitating particle may be magnetic, and step (d) may further comprise applying a magnetic field perpendicular to and below the non-permeable surface. The first and second colors may be yellow and blue or blue and yellow, respectively, and the combination of the first and second colors may be green; or wherein the first and second colors may be red and blue or blue and red, respectively, and the combination of the first and second colors may be purple; or wherein the first and second colors may be yellow and red or red and yellow, respectively, and the combination of the first and second colors may be orange. The capture particle may be located on the non-permeable surface, and steps (b) and (c) may be comprised in a single step of dropping the sample onto the non-permeable surface. Steps (b) and (c) may be reversed in order. The precipitating particle may produce an aggregate with the analyte and the capture particle, the aggregate being substantially incapable of movement to the droplet edge.

In yet another embodiment, there is provided a method for detecting an analyte in a sample comprising (a) providing a sample in a liquid form; (b) contacting the liquid sample with a capture particle that binds the analyte, wherein the capture particle is detectable when aggregated; (c) placing a drop of the liquid sample in step (b) on a non-permeable surface, wherein the surface is derivatized to bind the analyte; (d) incubating the surface under conditions promoting evaporation of the drop; (e) washing the surface; and (f) detecting the aggregate at the droplet edge when the analyte is present, or not detecting an aggregate at the droplet edge when the analyte is not present.

The capture particle may be located on the non-permeable surface, and steps (b) and (c) may be comprised in a single step of dropping the sample onto the non-permeable surface. Steps (b) and (c) may be reversed in order. The capture particle may be labeled. Alternatively, the capture particle may undergo a color change when aggregated. The analyte may be malarial pfHRP2.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects and features of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

(FIG. 7B) Images of overnight incubation with PLH.

FIG. 10—Sequence of pfHRP2 (SEQ ID NO: 1). The protein has 54 HH motifs, highlighted in red.

FIG. 11—Design of AuNP ligands. Top: NTA ligand. Bottom: AuNP stabilizing ligand.

(FIG. 15A) Ni(II)NTA AuNPs incubated with poly-L-histidine. (FIG. 15B) Ni(II)NTA AuNPs without poly-L-histidine.

FIG. 17—(FIG. 17A) Synthesis of Ni(II)NTA functionalized slides. (FIG. 17B) Ring geometry as a function of substrate. Ni-NTA functionalized polystyrene particles (Spherotech, 1.39 um diameter, $3.4 \times 10^6$ particles/µL) were deposited (4 µL) and evaporated on: (i) Ni(II)NTA functionalized glass (Xenopore Corp.), (ii) untreated glass, (iii) $NH_2$-functionalized glass, and (iv) polyethylene glycol functionalized glass (Microsurfaces, Inc.). All images are identically scaled. (FIG. 17C.) Titration of PLH on a Ni(II)NTA slide. Varying concentrations of PLH (10 µM-1 µM, left to right; control on right) was spotted onto the Ni(II)NTA slide. Next, the slide was incubated with Ni(II)NTA AuNPs for 15 minutes and washed.

FIGS. 18A-C—Aggregation profile of Ni(II)NTA AuNPs induced by PLH. (FIG. 18A) Upon addition of PLH, Ni(II)NTA gold nanoparticles aggregate, inducing a surface plasmon resonance shift from red to purple. UV-Vis spectra (FIG. 18B) and particle size profile (FIG. 18C) of Ni(II)NTA AuNPs incubated with PLH.

FIGS. 20A-D—Two potential protein interferents (Human Histidine-Rich Glycoprotein and Human Serum Albumin) found in serum. UV-Vis spectra and particle size profiles for Ni(II)NTA AuNPs titrated with Histidine-Rich Glycoprotein (FIGS. 20A-B) and Bovine Serum Albumin (FIGS. 20C-D).

FIGS. 22A-B—(FIG. 22A) SDS-PAGE gell of M(II) NTA polystyrene microspheres incubated with human serum. Protein was eluted from the microspheres upon addition of 500 nM imidazole. (FIG. 22B) Sustained capture of a fluorescently labeled HRP-II peptide mimic to M(II)NTA functionalized microspheres in the presence of 50 mM imidazole.

DETAILED DESCRIPTION OF THE INVENTION

I. Drop-Based Principles

In designing new diagnostic methods, there would be considerable advantages to an assay that is simple to perform, does not require instrumentation, is inexpensive to manufacture, is stable over a variety of environmental conditions, and can be readily interpreted by an unskilled end-user. The need for new approaches to rapid diagnostics for non-industrialized countries continues to be highlighted by medical organizations around the world. Most commercial tests suffer from extreme sensitivity to thermal storage conditions and poor performance at low antigen concentrations.

Figure 12:
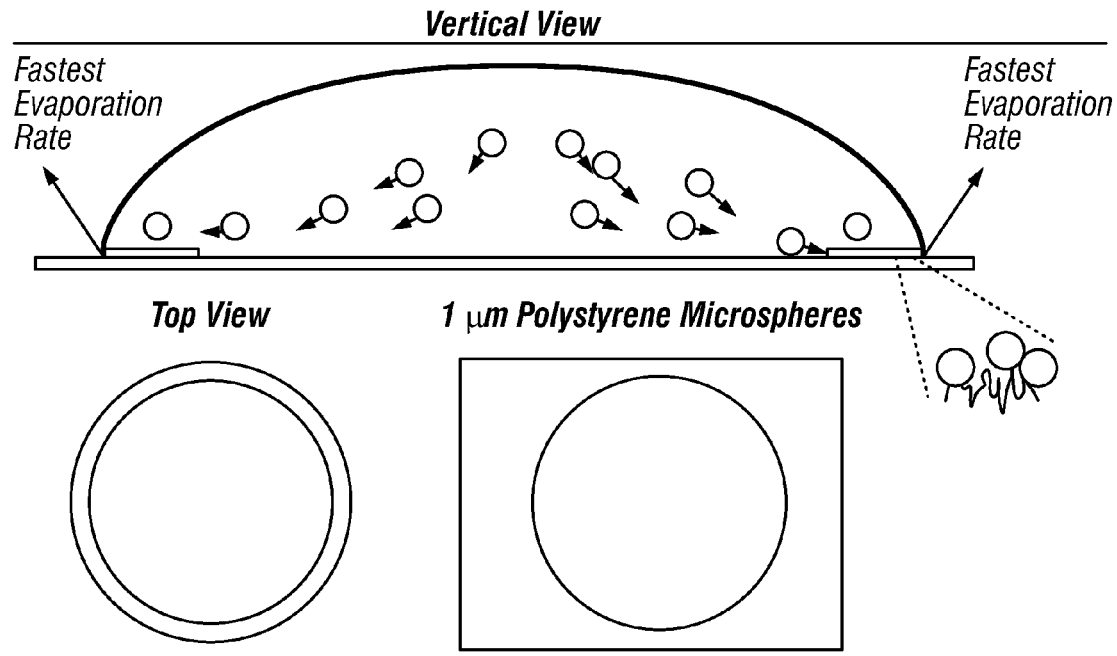
FIG. 12—Schematic of the coffee stain phenomenon.

The proposed method utilizes the phenomenon observed by Deegan and coworkers where fine particles in coffee generate a well defined peripheral ring when a droplet is dried on a glass surface (Deegan et al., 1997). As the droplet dries, evaporation occurs fastest at the drop edge. If pinning of the liquid to the surface occurs, then the droplet maintains morphology by capillary flow from the center of the drop toward the droplet edge, causing any solute to be transported and subsequently deposited at the edge of the droplet (FIG. 12).

The inventor proposes the avoidance of commercial diagnostic limitations by use of a simple alternative diagnostic design based on the aforementioned rapid, radial transport and deposition of small particles at the edge of an evaporating drop. This unconventional design incorporates three key features. First, unlike diffusion/lateral flow based assays, aggregate transport and concentration are achieved by the microfluidics of drop evaporation. Second, the visual results are produced by, e.g., a unique colorimetric property of particles. And third, the technology is thermally stable and does not depend on antibodies. The aggregation and microfluidic features represent a new approach for diagnostics that offers unique and promising alternatives to existing low resource formats.

These and other aspects of the invention described in greater detail below.

II. Assay Reagents

The present invention relies, in one aspect, on the use of a capture particle. The only requirements for the capture particle are that it (a) it is able to bind to an analyte in solution in a selective or specific fashion, and (b) that it will be subject to the fluid dynamics of a surface drop, as described by Deegan et al. (1997). Thus, in one aspect, the particle may be a capture agent, such as an antibody. In other embodiments, particularly for low molecular binding molecules, the capture particle will comprise a scaffold, such as a bead or nanoparticle, and the low molecular binding molecule attached thereto.

Differential evaporation rates (edge→center) are necessary to form a ring in an evaporating drop. The edge and center evaporation rates, both absolute and relative, determine speed of ring formation. Improving the differential rate can result in improved assay performance. This can be achieved by using a substrate that is semi-permeable/porous near the contact line thus enhancing evaporation rates at the edge of the drop.

A. Particles and Beads

In determining the appropriate binding molecule scaffold, a number of factors must be considered. These factors include size, ligand attachment strategy, stability, aggregation properties, and visibility to an end-user. The discussion below provides a list of suitable bead/particles that can be used in accordance with the present invention.

Particles. In certain embodiment, the present invention uses various compositions known generically as "particles." Particles can range in size from nanometers (so called nanoparticles) to those in the 10-100 micron size or larger. Particles are often spherical or round, but irregularly shaped particles are also known and useful in accordance with the present invention.

The particles may be made of glass, polystyrene, latex, metal, quantum dot, polymers, silica, metal oxides, ceramics, or any other substance suitable for binding to nucleic acids, or chemicals or proteins which can then attach to nucleic acids. The particles may be rod shaped or spherical or disc shaped, or comprise any other shape. The particles may be spectrally distinct by virtue of having a composition containing dyes or ratios or concentrations of one or more dyes or fluorochromes, or may be distinguishable by barcode or holographic images or other imprinted forms of particle coding.

The particles may be magnetic particles, allowing them to be attracted to the surface of the chamber by application of a magnetic field. Likewise, magnetic particles may be dispersed from the surface of the chamber by removal of the magnetic field. The magnetic particles are preferably paramagnetic or superparamagnetic. Paramagnetic and superparamagnetic particles have negligible magnetism in the absence of a magnetic field, but application of a magnetic field induces alignment of the magnetic domains in the particles, resulting in attraction of the particles to the field source. When the field is removed, the magnetic domains return to a random orientation so there is no interparticle magnetic attraction or repulsion. In the case of superparamagnetism, this return to random orientation of the domains is nearly instantaneous, while paramagnetic materials will retain domain alignment for some period of time after removal of the magnetic field.

Of particular suitability in the present invention are metal particles. The metal may, for example, be comprised of silver, antimony, bismuth, lanthanum, tin, thallium, titanium, cerium, iron, cadmium, chromium, nickel, manganese, cobalt, zinc or gold.

For example, citrate-stabilized AuNPs can serve as the ligand scaffold for a variety of reasons. Ligand exchange is simple and efficient with a thiolated ligand because the citrate molecules can be easily displaced. Specifically, 15 nm AuNPs exhibit a unique surface Plasmon resonance absorption at 520 nm, allowing for visible detection in a reaction solution. Also, at this size, these particles can also be easily separated from a reaction solution using centrifugation, allowing for simple purification of the AuNPs. When aggregation is induced by target addition, the aggregates exhibit a different surface Plasmon absorbance, which can be used as a visible indicator of target binding. Unlike antibodies used in the traditional RDTs, ligand-stabilized AuNPs are highly stable over a wide range of temperatures. Further stabilization can be achieved by adding a secondary stabilizing ligand that serves primarily to stabilize the construct while maintaining the integrity of the ligand-target interaction.

In designing the capture ligand, a number of factors will be considered. These factors include affinity to the target, attachment strategy, alkane spacer length, and ethylene glycol length. As seen above, pfHRP2 binds selectively to $Ni^{2+}$-, $Cu^{2+}$- and Zn-NTA agarose affinity columns with higher affinity than other enzymes found in blood or serum, including human serum albumen, transferrin, α2-macroglobulin, and histidine-rich glycoprotein (Panton et al., 1989; Ghimire et al., 2003). Thus, a ligand containing a Cu-NTA or Ni-NTA is ideal for specific binding of pfHRP2. Also, gold-thiol chemistry is well established (Love et al., 2005), so the use of gold nanoparticles as the scaffold would allow for ligand attachment via a thiol modification on the opposite end of the ligand. Previous studies have shown that alkane spacers of 11 or larger can serve as a suitable spacer between Cu-NTA or Ni-NTA and the gold surface (Barton et al., 2006). Tri-ethylene glycol spacers have also been shown supplement the alkane spacer by improving solubility of AuNPs, as well as minimize non-specific protein binding (Scmitt et al., 2000; Mrksich et al., 1996; Palegrosdemange et al., 1991; Prime & Whiteside, 1991; Sigal et al., 1996). Therefore, a thiolated NTA ligand that contains a tunable alkane chain and triethylene glycol spacer was synthesized (FIG. 11).

After synthesis of the NTA ligand, it will be attached to the gold nanoparticles using methods previously established in the lab. Briefly, combinations of NTA ligand and AuNP stabilizing will be conjugated to 15 nm gold nanoparticles by overnight incubation to allow ligand exchange. Ratios of NTA from 10-100% will functionalized to the AuNPs to determine the ideal NTA concentration. The particles will be washed by centrifugation and the supernatant removed. After resuspension in 0.1 M HEPES buffer pH 7.4, the particles will be charged with $Ni^{2+}$ for 30 minutes. Final centrifugation and washing steps will be conducted to remove any excess reactants. The Ni-NTA AuNPs will then be resuspended in HEPES buffer and be ready for use. Quality control of the Ni-NTA AuNPs will be assessed by UV-Vis spectroscopy, dynamic light scattering, Zeta potential measurements, and TEM analysis. The number of Ni(II) containing ligands per AuNP will be calculated by ICP-AES, which determines the relative concentration of Ni(II) and Au found in the reaction solution.

Beads. Beads are considered to be a particular kind of particle. Such beads include those produced by Luminex (Austin Tex.) or MicroMod (Germany), made of polystyrene, Dyanbeads®, produced by Invitrogen, or nylon beads.

B. Surfaces

Flat, non-permeable surfaces for deposition of the drop in accordance with the present invention can be made of, or coated with, virtually any type of material that provides the necessary fluid dynamics. Such materials include glass, plastic (e.g., polystyrene) or metal. Such surfaces may be derivatized to facilitate the use of different solvent, capture agents and detection methods. Of particular use are glass or plastic slides.

Visible detection is essential for low cost and simple diagnostic uses. In order to achieve this goal, surfaces will need to be modified for the particular antigen-bead/particle system being used. For example, a number of factors must be considered when developing a particular drop surface, such as for the aggregated target-AuNP construct. These factors include: capture ligand composition, and surface hydrophilicity/hydrophobicity. The capture ligand must specifically bind the target-AuNP aggregate without non-specifically binding to unreacted AuNPs. Ni-NTA ligands are ideal surface ligands because they are equivalent to the AuNP ligands and should not introduce any additional non-specific binding. Spacer ligands containing ethylene glycol will also be introduced to reduce non-specific binding and help to tune the hydrophilicity of the surface. The surface has to "pin" the liquid droplet so that solute will be deposited at the drop edge, forming a ring and not distributed throughout the drop-surface interface.

Figure 13:
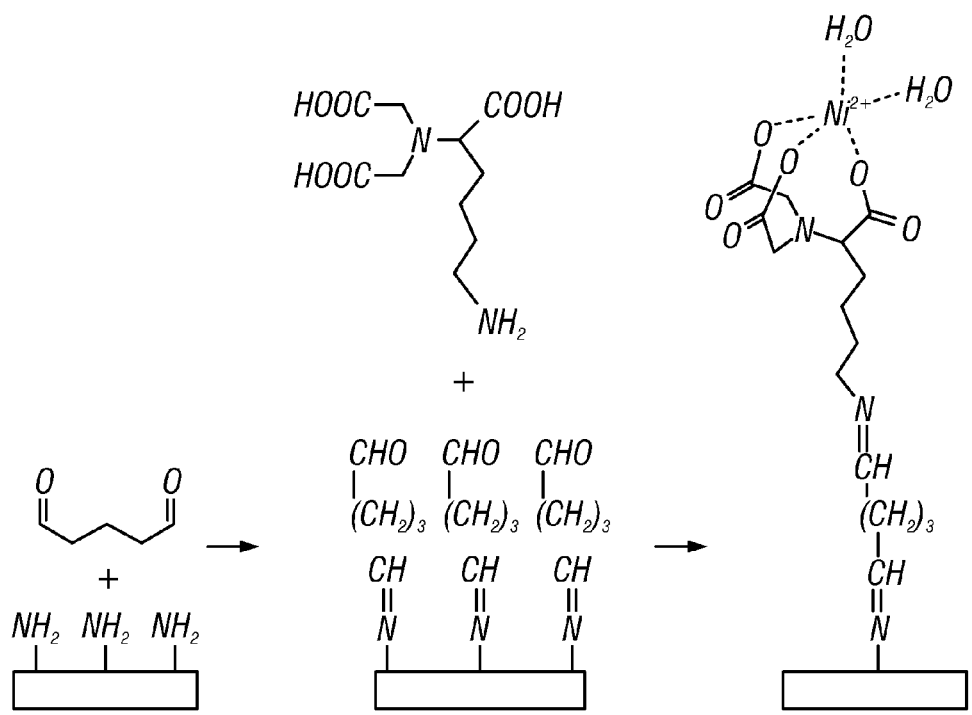
FIG. 13—Synthesis design for Ni-NTA-functionalized glass slides (Tachibana et al., 2006).

Using contact angle measurements, the relative surface charge of the NTA glass slide will be calculated. Ni-NTA slides will also be synthesized by crosslinking Nα,Nα-Methylcarboxy-L-lysine to amine-functionalized slides and compared to the commercial product by contact angle measurements to ensure similar surface properties (FIG. 13).

Glass slides or coverslips will first be cleaned using Piranha solution. After washing the slides with water or ethanol and drying in an 80° C. oven, the slides will be functionalized with 3-Aminopropyltriethoxysilane (APTES) to afford an amine-coated slide. Activation of the slides with glutaraldehyde, followed by the addition Nα,Nα-Methylcarboxy-L-lysine will provide the NTA motif necessary for $Ni^{2+}$ chelation. After washing with water, the activated slides will be incubated with Ni(II) to afford Ni-NTA-functionalized slides. The surface charge of the slides will then be determined by contact angle measurements.

Figure 25:
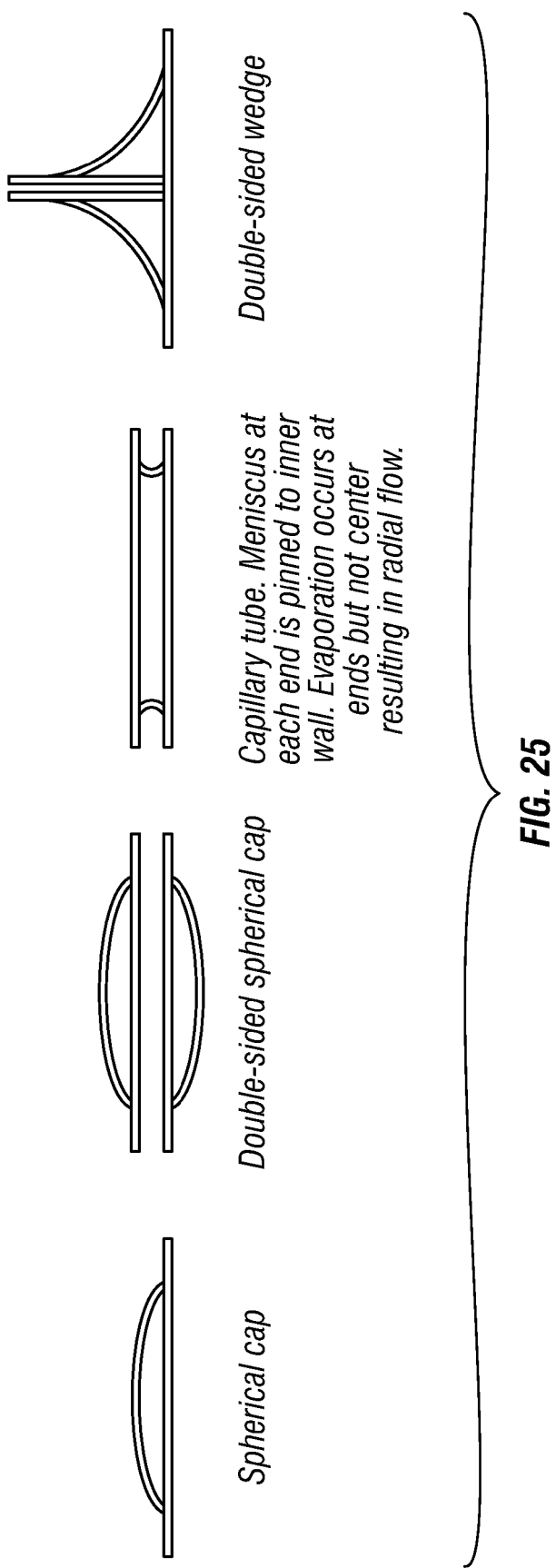
FIG. 25—Alternative surface geometries.

Various alternative geometries are shown in FIG. 25, such as double-sided spherical cap (around a rod), meniscus within a capillary tube, and double-sided wedge (e.g., using a microarray pen to deposit the fluid, thereby creating an apron of fluid around the pen), and are compared to a drop on a flat surface (spherical cap).

C. Analyte Binding Agents

Analyte binding agents in accordance with the present invention include virtually any type of agent that is capable of interacting in a selective or specific manner with a cognate binding partner. Such agents include proteins, chemicals, nucleic acids, metals, or carbohydrates (e.g., lectins). In particular, the protein may be an antibody, a receptor, an antigen, or a fragment of any of the foregoing.

D. Alternative Methods

In addition to the design embodiments described above, there exist others embodiment in which substrate surface-antigen or particle-antigen interaction (or both) promotes or inhibits at least one necessary condition for ring formation, namely, contact line pinning or sufficient substrate hydrophilicity. If a requisite condition for ring formation is inhibited as a result of having antigen present in the sample, then the ring will not form or will results in a structure sufficiently different than the ring structure that results if antigen is not present. In this case, the presence of a ring or the structure of the ring serves as the visual indicator rather than ring color. This design could be implemented as a one-particle assay (see below).

For example, the substrate may be surface-modified with a surfactant polymer containing antigen-binding elements. If the antigen is not present, the surfactant prevents the contact line from pinning and thus no ring develops. If the antigen is present, the contact line pins due to the antigen crosslinking particles in solution to the substrate. With the pinned contact line condition satisfied, a ring is generated upon evaporation.

Alternatively, the surface chemistry of particles in solution may be designed such that the particle surface chemistry is altered in the presence of antigen in such a way so as to promote or inhibit contact line pinning or to change the contact angle sufficiently to alter ring structure.

Tunable hydrophobic properties of both substrate and particle surfaces have been demonstrated in other implementations (Hoy et al., 2010; Nyfors et al., 2009).

III. Assay Formats

The basic concept involves the use of dectable (e.g., visible) changes in the ring structure at the edge of an evaporated drop of fluid to diagnose, for example, an infection or cancer in a subject, or to detect environmental pollutants, toxins, illegal drugs, etc., in virtually any sample. In one design, the aggregation and capture of antigens from a drop of patient's blood deposited and dried on a pre-prepared glass slide will produce a color change at the edge of the drop if there is an infection. The essence of this design combines the microfluidic behavior of an evaporating drop with a simplified analog of a liquid-phase ELISA.

Numerous formats are possible, and the following discussion is merely provided as an exemplary embodiment.

A. One Particle

Various one-bead assays are envisioned. Here, the single particle that binds to an analyte will be transported to the edge of a drop via microfluidic behavior. Detection of the analyte is then effected through one of several various options. First, the aggregation of particles (due to presence of analyte) in solution may result in a color change relative to non-aggregated material. Here, the mere collection of the aggregated species at the edge of the drop permits detection of the color change. Second, one may actually perform a secondary detection step at the edge of the drop, where the capture particle has merely served to concentrate the analyte in one spot. It also may be useful to incorporate a secondary binding reagent on the flat surface to capture the analyte, and at the same time retain the capture particle which is detected through various different approaches.

Figure 9:
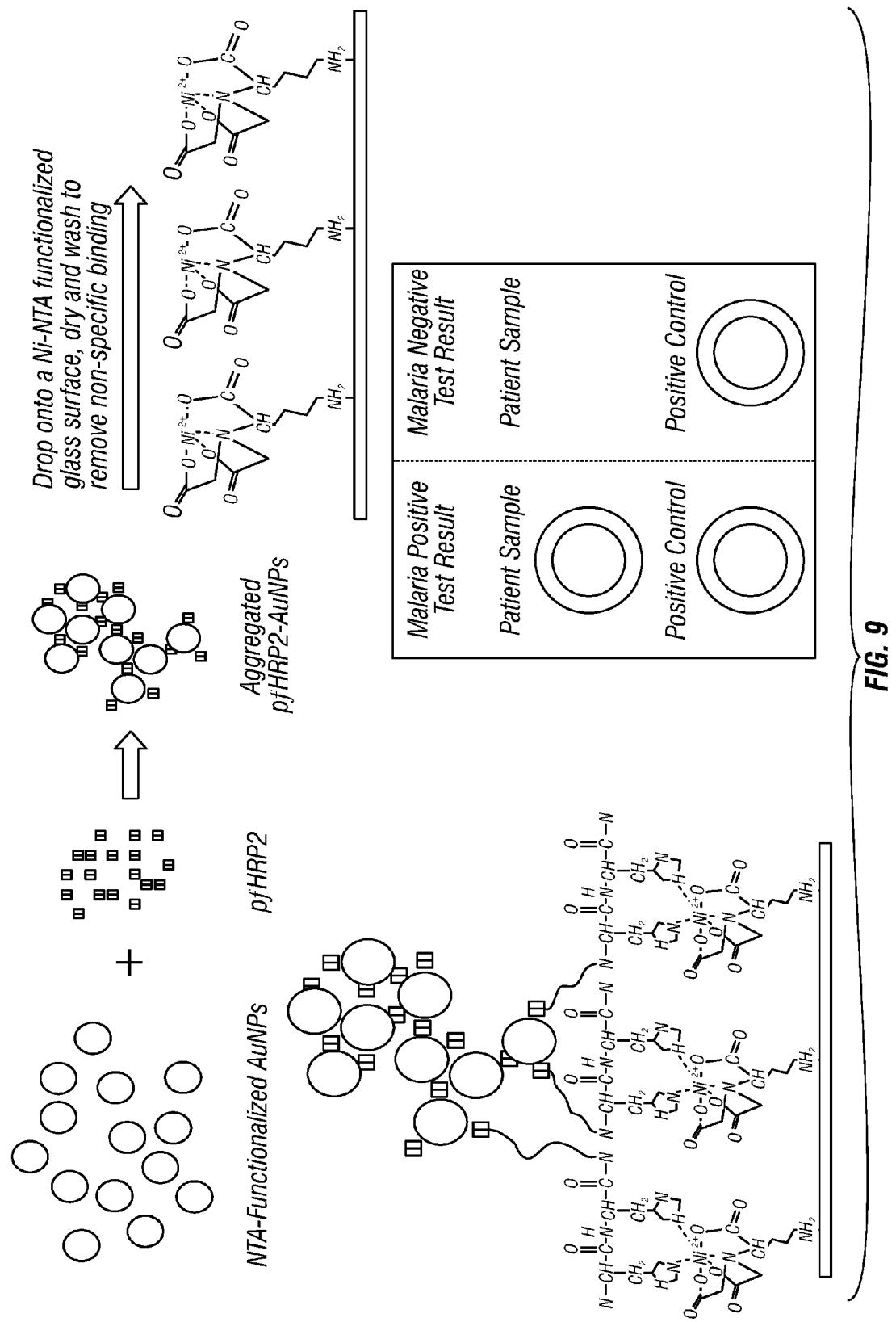
FIG. 9—Proposed malaria diagnostic design.

In one embodiment, the inventors propose the development of a new rapid diagnostic test for malaria detection that combines the aggregation behavior of ligand-stabilized AuNPs and the deposition behavior of small volume colloidal-containing droplets on glass slides (FIG. 9). The resulting diagnostic will consist of Ni-NTA-containing ligands coordinated to the surface of 15 nm AuNPs via thiol-Au bonds. The affinity of pfHRP2 towards Ni-NTA results in crosslinking of multiple AuNPs with the enzyme, causing irreversible aggregation. When a small volume of the reaction mixture is then spotted on a Ni-NTA functionalized glass slide, the presence of pfHRP2 induces binding of the aggregate to the slide, leaving a distinct purple ring even after extensive washing with a blocking buffer containing imidazole. This diagnostic will maintain many of the advantages of the antibody-containing RDTs, but also provide more stability and reproducibility in harsh environments.

Much like the current RDT strategies, the proposed design targets pfHRP2. Briefly, pfHRP2 is a 67 kDa protein that consists of 34% histidine assembled in multiple repeats of AHH and AHHAAD (FIG. 10). It is the primary target for current RDTs because of its high concentration in host serum, blood, and saliva (Chiodini et al., 2007). With its extraordinarily high content of histidine, pfHRP2 binds selectively to $Ni^{2+}$ and Zn-NTA agarose affinity columns with higher affinity than other enzymes found in blood or serum, including human serum albumin, transferrin, α2-macroglobulin, and histidine-rich glycoprotein (HRG) (Panton et al., 1989; Ghimire et al., 2003). Recent studies have also shown that histidine-tagged proteins bind to NTA ligands functionalized onto gold (Barton et al., 2006; Brinas et al., 2008; De et al., 2009; Hainfield et al., 1999; Lee et al., 2009), polystyrene microspheres (Lauer & Nolan, 2002), and quantum dots (Gupta et al., 2008). The inventors propose that this high binding affinity can be replicated for pfHRP2 with NTA-functionalized gold nanoparticles (NTA AuNPs).

B. Two Particles

Two-particle systems can be employed. Such systems may comprise, for example, an antibody as the capture particle and a precipitating particle. In the absence of analyte, the antibody will move to the drop edge and be detected by a label, or by secondary detection (e.g., labeled protein A). In the presence of analyte, the precipitating particle and the capture particle both bind to the antigen, resulting in aggregation and precipitation—thus precluding antibody build up at the drop edge.

C. Three Particles

Figure 14:
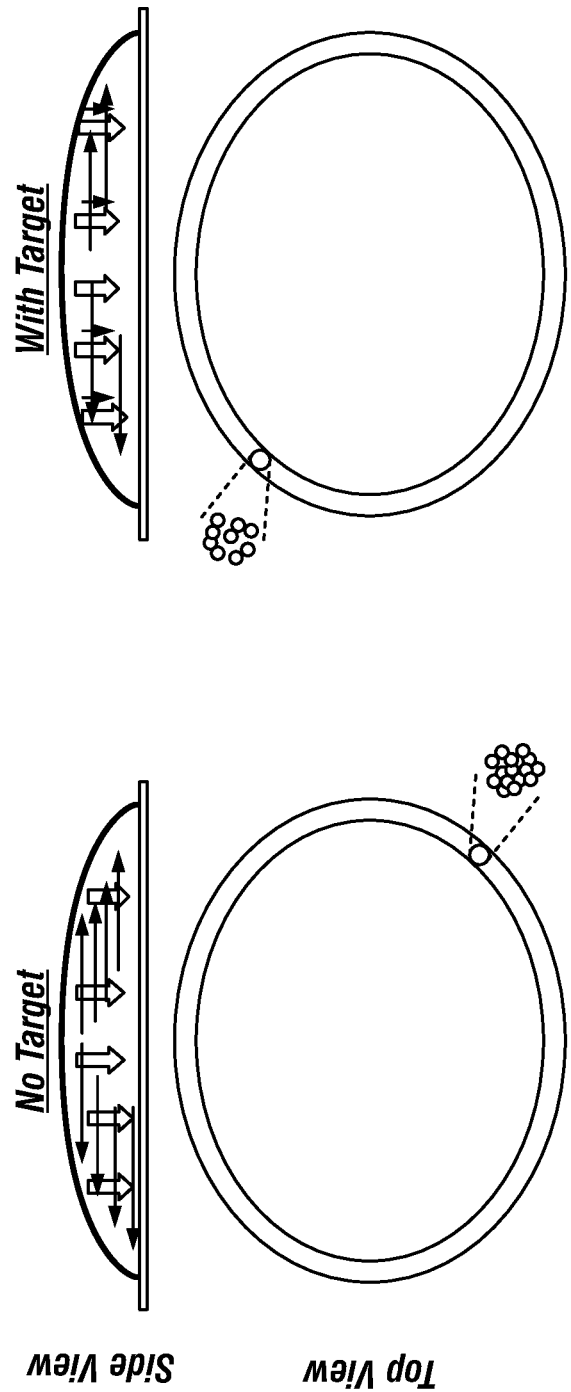
FIG. 14—Change in "coffee ring" stain produced by the presence of an infective agent.

A more complex three-particle system can utilize two complementary colored particles—one of them being a capture particle and the other being a positive control particle. In the absence of analyte, these particles will move to the edge of the drop and their combined color is detected. However, in the presence of analyte the capture particle is aggregated, through binding of the analyte, to a precipitating particle, which also binds analyte. This causes the capture particle to drop out of solution (either by weight or application of a magnetic field), and only the positive control particle will move to the drop edge. As such, the color will be distinct from that when the capture particle also is at the edge. This sort of assay is shown in FIG. 14.

D. Multiplexing

By increasing the number of differentially labeled beads, one could provide for a multiplexed reaction looking for different analytes simultaneously. As discussed below, there are a large number of different labels that can be employed, and thus one might look at 2, 3, 4, 5, 6, 7, 8, 9, 10, 11, 12, 13, 14, 15, 16, 17, 18, 19, 20, 25, 30 or more analytes at once, using 4-32 beads or more.

E. Labels

Luminescent labels. Chemical luminescent labels include luminol and cyalume, both of which are activated by hydrogen peroxide. Bioluminescent labels include firefly luciferase, *Renilla* luciferase, and bacterial luciferase.

Fluorescent labels. Fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

*Aequorea victoria* are brightly luminescent jellyfish, with glowing points around the margin of the umbrella. Light arises from yellow tissue masses that each consist of about 6000-7000 photogenic cells. The cytoplasm of these cells is densely packed with fine granules that contain a Ca++ activated photoprotein, aequorin, that emits blue-green light, and an accessory green fluorescent protein (GFP), which accepts energy from aequorin and re-emits it as green light. GFP is an extremely stable protein of 238 amino acids, stable in neutral buffers up to 65° C., and displaying a broad range of pH stability from 5.5 to 12. The protein is intensely fluorescent, with a quantum efficiency of approximately 80% and molar extinction coefficient of $2.2 \times 10^4$ cm-1 M-1 (after correction for the known molecular weight). GFP fluoresces maximally when excited at 400 nm with a lesser peak at 475 nm, and fluorescence emission peaks at 509 nm. Since the purification and cloning of the GFP from *Aequorea Victoria*, similar fluorescent proteins have been isolated and cloned from many other species including dynoflagelates, sea pens, and reef corals.

Two variants of the *Aequorea victoria* GFP, cyan fluorescent protein (CFP) and yellow fluorescent protein (YFP), have special fluorescence excitation and emission properties that are well suited to measurement of close molecular distances. Thus, variants of this type have been the most widely used for FRET experiments. When these two molecules are positioned at distances closer than 7 nm of each other, energy transfer can occur from the excited state of the donor molecule (CFP), to the unoccupied excited state of the acceptor molecule (YFP) by a process commonly referred to as fluorescence (or Förster) resonance energy transfer (FRET). FRET between CFP and YFP can be detected using a wide variety of spectroscopic and fluorescence microscopy techniques and is often used to report protein-protein interactions or changes in the conformation state of a peptide or protein. Since the efficiency of FRET is directly related to the spectroscopic properties of both the donor and acceptor molecules, improvements can be made to the fluorescence properties of the fluorophores, such as to increase both the FRET efficiency and the chances of successful detection. FRET has also been used to quantify association of a protein of interest with an organelle (Chiu et al., 2002). As more fluorescent proteins are developed, other FRET pairs are being tried, such as the CFP to an Orange FP from reef coral, called mKO (Karasawa et al., 2004). One of the strengths of the present invention is that it is broadly applicable to any pair of fluorescent proteins that have spectral properties sufficient to generate FRET.

The gene of the green fluorescent protein has been isolated and its sequence has also been determined (Prasher et al., 1992). There have also been numerous reports of amino acid sequences of other fluorescent proteins or their mutants, for example, as described in Tsein (1998) and the literature cited therein. Fluorescent proteins include green fluorescent protein, red fluorescent protein, yellow fluorescent protein, GFP, BFP, CFP, YFP, EGFP, EYFP, Venus, Citrine, phiYFP, copGFP CGFP, ECFP, Cerulean, CyPet, T-Sapphire, Emerald, YPet, AcGFP1, AmCyan, AsRed2, dsRed, dsRed2, dsRed-Express, EBFP, HcRed, ZsGreen, ZsYellow, J-Red, TurboGFP, Kusabira Orange, Midoriishi Cyan, mOrange, DsRed-monomer, mStrawberry, mRFP1, tdTomato, mCherry, mPlum, and mRaspberry.

The term "cyan fluorescent protein (CFP)" as used herein is defined as any fluorescent protein with an absorption maximum between 420 and 460 nm, and a fluorescence maximum between 460 and 500 nm. These proteins have mainly been derived from the wild-type *Aequoria* GFP with a Y66W mutation, resulting in a primary excitation peak at ~434 nm with minor excitation maxima at ~452 nm, and a primary emission peak is 477 nm with minor shoulder at ~505 nm (Heim et al., 1994). Other fluorescent proteins are termed "green fluorescent protein (GFP)", meaning proteins with absorption maxima between 480 and 500 nm and fluorescence maxima between 500 and 515 nm, and "yellow fluorescent protein (YFP)" meaning proteins with absorption maxima between 500 and 520 nm and fluorescence maxima between 515 and 535 nm.

Colorimetric labels. o-Phenylenediamine, ABTS and pNPP are all colorimetric substrates for hydrogen peroxidase.

Enzyme labels. Examples of suitable enzymes include urease, alkaline phosphatase, (horseradish) hydrogen peroxidase or glucose oxidase.

Radiolabels. Radioactive isotopes for diagnostic application include astatine$^{211}$, $^{14}$-carbon, $^{51}$chromium, $^{36}$-chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium[186], rhenium[188], [75]selenium, [35]sulphur, technicium[99m] and/or yttrium[90].

F. Detection Methods

One of the central advantages of the present invention is the use of simple and inexpensive detection methods that do not require sophisticated equipment or trained personnel. However, the present assays also are amenable to such more sophisticated procedures, which are specifically contemplated to be included herein.

Visual. Perhaps the most straightforward detection method is visible. Visible detection may rely on a color (presence or absence), color change, luminescence, or fluorescence. The present invention contemplates that the ring-like product produced from drop evaporation will provide a readily reconginzable feature that permits home and field use of the assays with minimal instruction (i.e., package inserts with instructions and diagrams).

Light Microscopy. Light or optical microscopy involves passing visible light transmitted through or reflected from the sample through a single or multiple lenses to allow a magnified view of the sample. The resulting image can be detected directly by the eye, imaged on a photographic plate or captured digitally. The single lens with its attachments, or the system of lenses and imaging equipment, along with the appropriate lighting equipment, sample stage and support, makes up the basic light microscope. The most recent development is the digital microscope which uses a CCD camera to focus on the exhibit of interest. The image is shown on a computer screen since the camera is attached to it via a USB port, so eye-pieces are unnecessary.

Bright field microscopy is the simplest of all the light microscopy techniques. Sample illumination is via transmitted white light, i.e., illuminated from below and observed from above. Limitations include low contrast of most biological samples and low apparent resolution due to the blur of out of focus material. The simplicity of the technique and the minimal sample preparation required are significant advantages.

The use of oblique (from the side) illumination gives the image a 3-dimensional appearance and can highlight otherwise invisible features. A more recent technique based on this method is Hoffmann's modulation contrast, a system found on inverted microscopes for use in cell culture. Oblique illumination suffers from the same limitations as bright field microscopy (low contrast of many biological samples; low apparent resolution due to out of focus objects), but may highlight otherwise invisible structures.

Dark field microscopy is a technique for improving the contrast of unstained, transparent specimens. Dark field illumination uses a carefully aligned light source to minimize the quantity of directly-transmitted (unscattered) light entering the image plane, collecting only the light scattered by the sample. Dark field can dramatically improve image contrast—especially of transparent objects—while requiring little equipment setup or sample preparation. However, the technique does suffer from low light intensity in final image of many biological samples, and continues to be affected by low apparent resolution.

Rheinberg illumination is a special variant of dark field illumination in which transparent, colored filters are inserted just before the condenser so that light rays at high aperture are differently colored than those at low aperture (i.e., the background to the specimen may be blue while the object appears self-luminous yellow). Other color combinations are possible but their effectiveness is quite variable.

Dispersion staining is an optical technique that results in a colored image of a colorless object. This is an optical staining technique and requires no stains or dyes to produce a color effect. There are five different microscope configurations used in the broader technique of dispersion staining. They include brightfield, Beckè line, oblique, darkfield, phase contrast, and objective stop dispersion staining.

When certain compounds are illuminated with high energy light, they then emit light of a different, lower frequency. This effect is known as fluorescence. Often specimens show their own characteristic autofluorescence image, based on their chemical makeup.

This method is of critical importance in the modern life sciences, as it can be extremely sensitive, allowing the detection of single molecules. Many different fluorescent dyes can be used to stain different structures or chemical compounds. One particularly powerful method is the combination of antibodies coupled to a fluorochrome as in immunostaining Examples of commonly used fluorochromes are fluorescein or rhodamine. The antibodies can be made tailored specifically for a chemical compound. For example, one strategy often in use is the artificial production of proteins, based on the genetic code (DNA). These proteins can then be used to immunize rabbits, which then form antibodies which bind to the protein. The antibodies are then coupled chemically to a fluorochrome and then used to trace the proteins in the cells under study.

Highly-efficient fluorescent proteins such as the green fluorescent protein (GFP) have been developed using the molecular biology technique of gene fusion, a process which links the expression of the fluorescent compound to that of the target protein. This combined fluorescent protein is generally non-toxic to the organism and rarely interferes with the function of the protein under study. Genetically modified cells or organisms directly express the fluorescently-tagged proteins, which enables the study of the function of the original protein in vivo.

Since fluorescence emission differs in wavelength (color) from the excitation light, a fluorescent image ideally only shows the structure of interest that was labeled with the fluorescent dye. This high specificity led to the widespread use of fluorescence light microscopy in biomedical research. Different fluorescent dyes can be used to stain different biological structures, which can then be detected simultaneously, while still being specific due to the individual color of the dye. To block the excitation light from reaching the observer or the detector, filter sets of high quality are needed. These typically consist of an excitation filter selecting the range of excitation wavelengths, a dichroic mirror, and an emission filter blocking the excitation light. Most fluorescence microscopes are operated in the Epi-illumination mode (illumination and detection from one side of the sample) to further decrease the amount of excitation light entering the detector.

Fluorescence microscopy is extremely powerful due to its ability to show specifically labeled structures within a complex environment and also because of its inherent ability to provide three dimensional information of biological structures. Unfortunately this information is blurred by the fact that upon illumination all fluorescently labeled structures emit light no matter if they are in focus or not. This means that an image of a certain structure is always blurred by the contribution of light from structures which are out of focus. This phenomenon becomes apparent as a loss of contrast especially when using objectives with a high resolving power, typically oil immersion objectives with a high numerical aperture.

Fortunately though, this phenomenon is not caused by random processes such as light scattering but can be relatively well defined by the optical properties of the image formation in the microscope imaging system. If one considers a small fluorescent light source (essentially a bright spot), light coming from this spot spreads out the further out of focus one is. Under ideal conditions this produces a sort of "hourglass" shape of this point source in the third (axial) dimension. This shape is called the point spread function (PSF) of the microscope imaging system. Since any fluorescence image is made up of a large number of such small fluorescent light sources the image is said to be "convolved by the point spread function."

Knowing this point spread function means that it is possible to reverse this process to a certain extent by computer based methods commonly known as deconvolution microscopy. There are various algorithms available for 2D or 3D deconvolution. They can be roughly classified in non-restorative and restorative methods. While the non restorative methods can improve contrast by removing out of focus light from focal planes, only the restorative methods can actually reassign light to it proper place of origin. This can be an advantage over other types of 3D microscopy such as confocal microscopy, because light is not thrown away but reused. For 3D deconvolution one typically provides a series of images derived from different focal planes (called a Z-stack) plus the knowledge of the PSF which can be either derived experimentally or theoretically from knowing all contributing parameters of the microscope.

Automated Detection. A variety of automated devices for reading colorimetric, fluorescent and chemilluminescent reactions are available from commercial sources. The machines, often used for reading of large throughput assays using multi-well plates, can be adapted for use with the assays of the present invention. The output may advantageously be transferred to a computer for further analysis and manipulation. In particular, one detection embodiment involves spotting of the material onto a cell phone camera lens, or on a platform (e.g., disposable) that can be affixed adjacent to the camera lens. Then, simply by taking a picture, one can obtain a digital image of the material which optionally maybe analyzed by (a) emailing the image to a computer with image processing software, or (b) image processing software loaded onto the cell phone itself.

FRET. Förster Resonance Energy Transfer (FRET) is a phenomenon in which the excited-state energy in one molecule (called the donor) is transferred to another molecule by a radiationless coupling. This mechanism was first correctly described by Förster, and differs from other types of energy transfer, such as electron sharing (Dexter) or trivial transfer (emission of a photon from the donor and reabsorption by the acceptor). The Dexter mechanism requires the two molecules to be in physical contact, while trivial transfer is a very low probability. In contrast, the Förster mechanism exhibits a high probability when the two molecules are within the Förster radius, which is defined for any given pair of fluorophores.

The overall FRET efficiency depends on the Förster radius, and is determined by several factors and is directly related to the amount of overlap between the absorption spectra of the acceptor molecule and the emission spectra of the donor molecule. The amount of FRET also depends on the alignment of the donor and acceptor molecules, although most biological systems are not ridgidly aligned. The FRET efficiency is also affected by the ability of the acceptor molecule to absorb light, as indicated by its molar extinction coefficient, and the overall stability of the excited state of the donor molecule, as indicated by the probability that absorption will lead to fluorescence (quantum yield) and the lifetime of the excited state.

FRET between two different fluorophores can be assayed by several methods: looking at the change in color of the fluorescence, measuring the fluorescence lifetime of the donor, examining the changes upon photobleaching either the donor or acceptor, or as the inventors show here: by measuring the fluorescence polarization of the acceptor. Regardless of the approach, most of these assays share common features of the instrumentation.

The types of the microscope used to measure FRET can be suitably selected depending on the purpose. If frequent observations are necessary for monitoring a time course of the changing, conventional incident-light fluorescent microscope is preferred. If resolution is to be increased as in the case where detailed intercellular localization is to be monitored, confocal laser microscope is preferred. As a microscope system, an inverted microscope is preferred for most live cell measurements in view of keeping the physiological state of cell and preventing contamination. When an upright microscope is used, a water immersion lens can be used in the case of using lens of high power.

The filter set can be suitably selected depending on the fluorescent wave length of the fluorescent protein. For the observation of GFP, it is preferred to use a filter with excitation light of about 470-490 nm and fluorescent light of about 500-520 nm. For the observation of YFP, it is preferred to use a filter with excitation light of about 490-510 nm and fluorescent light of about 520-550 nm. For the observation of CFP, it is preferred to use a filter with excitation light of about 425 nm and fluorescent light of about 460-500 nm. For the purposes of the present invention, there are no specific requirements in terms of microscopes and filters, except that it would be useful to minimize the use of depolarizing elements in the light path. Microscope manufacturers all market strain-free optics for polarized light measurements in transmission and reflection microscopy, and such optics would be helpful for these polarized fluorescence measurements as well.

Moreover, when time course observation is carried out in living cells by using a fluorescent microscope, the cells should be photographed in a short period, and therefore a high sensitive cooled CCD camera is used. By using a cooled CCD camera, thermal noise can be decreased by cooling CCD, and weak fluorescent image can be clearly acquired by exposure of short period. Confocal microscopes can also be used for live cell imaging, as long as care is taken to minimize the exposure times.

The issues that are particular to this invention involve the polarization of the donor excitation and the acceptor emission. The steady-state polarization of a fluorophore is directly related to its rotational diffusion and the length of its fluorescence lifetime. The shorter the lifetime and slower the rotation, the more highly polarized the fluorescence. The amount of polarization of the fluorescence is expressed as the anisotropy of the fluorophore. The maximum value is 0.4 for single photon excitation, and GFPs in solutions such as the cell cytoplasm have a steady-state anisotropy value of about 0.3. A highly depolarized fluorescence signal will have an anisotropy value less than 0.1. For two-photon excitation, fluorescence excitation is even more highly polarized, and the theoretical maximum is 4/7 (or approximately 0.57). Generally, anisotropy values above 0.3 are considered highly polarized, and values less than 0.2 are considered depolarized.

What is measured in the current invention is a combination of fluorescence arising from FRET and the crosstalk excitation of the acceptor, so the presence of FRET would be indicated absolutely by a general decrease in the anisotropy as a function of the increasing proportion of FRETing molecules. With GFPs, this works well since the anisotropy starts at a rather high 0.3 and decreases from there. The absolute value of the steady-state anisotropy is ultimately less important than the fact that it decreases in the presence of FRET.

One of the strengths of the current invention is that almost any existing fluorescence microscope of high-throughput screening system can be easily modified to use polarization as a high-contrast FRET assay. All that is required is a polarizer in the excitation path and another in the emission collection optics. In practice, both of these should be rotatable to allow the collection of all four combinations of excitation and emission polarizations as described in the example below (vertical excitation—vertical emission; vertical excitation—horitzontal emission; horitzontal excitation—vertical emission; horitzontal excitation—horitzontal emission). The polarization behavior of light in a microscope is well understood through many years of the use of polarized light in transmission and reflection microscopy to examine material structure, and through the use of polarization in optical contrast methods such as Nomarski DIC. Polarization of fluorescence has not yet been used extensively in microscopy as a contrast mechanism. It is known, however, how to correct from the effects of focusing polarized light through the objective lens of the microscope (Axelrod, 1989). These corrections have been used to assay homo-energy transfer in fluorescence microscopy (Blackman et al., 1996; Rocheleau et al., 2003), and can be easily applied to the current invention.

IV. Samples and Diagnostic Targets

A. Samples

Samples can come from a wide variety of sources. In one aspect, the sample is derived from a living organisms, include a plant, animal (veterinary uses) or human. Such samples may involve solid material such as feces or tissues (including biopsies), tissue extracts, or fluids, including body fluids such as saliva, sputum, tears, blood, serum, plasma, urine, exudate, transudate, spinal fluid, semen or nasal discharge. Such samples may be solubilized or diluted, as needed, to perform the assays of the present invention. Solvents for use in solubilizing or diluting samples include water, acetone, methanol, toluene, ethanol or others.

Other samples, are manufactured, industrial or environmental, and may or may not contain living cells or organisms. Such sample may include soil, water, foodstuffs, alcoholic beverages, building products, bulk chemicals or reagents, including drugs. Again, such samples may be solubilized or diluted, as needed, to perform the assays of the present invention.

B. Targets

Autoimmune Antigens or Antibodies Thereto. Autoimmune diseases can be generally classified as antibody-mediated, T-cell mediated, or a combination of antibody-mediated and T-cell mediated. Thus, antibodies or T-cell receptors can be identified with specificity to a variety of endogenous antigens. Such auto-antibodies (e.g., anti-nuclear antibodies) may be implicated in various disease including insulin-dependent (type I) diabetes mellitus, rheumatoid arthritis, multiple sclerosis, systemic lupus erythematosus (SLE), and inflammatory bowel disease (i.e., Crohn's disease and ulcerative colitis). Other autoimmune diseases include, without limitation, alopecia greata, acquired hemophilia, ankylosing spondylitis, antiphospholipid syndrome, autoimmune hepatitis, autoimmune hemolytic anemia, cardiomyopathy, celiac sprue dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, discoid lupus, essential mixed cryoglobulinemia, fibromyalgia, fibromyositis, Guillain-Barr syndrome, idiopathic pulmonary fibrosis, idiopathic thrombocytopenic purpura, IgA nephropathy, juvenile arthritis, lichen planus, myasthenia gravis, polyarteritis nodosa, polychondritis, polyglandular syndromes, dermatomyositis, primary agammaglobulinemia, primary biliary cirrhosis, psoriasis, Raynaud's phenomena, Reiter's syndrome, sarcoidosis, stiff-man syndrome, Takayasu arthritis, temporal arteritis/giant cell arteritis, uveitis, vasculitis, and vitiligo.

In particular autoimmune diseases, antibodies to self antigens are frequently observed. For example for systemic lupus erythematosus autoantibodies have been described to single-stranded and double-stranded DNA or RNA (Vallin et al., 1999; Hoet et al., 1999; yen Venrooij, 1990). The levels of autoantibodies found in the serum of autoimmune patients very often are found to correlate with disease severity. The pattern of autoantibodies that arise, e.g., in human SLE, suggest that intact macromolecular particles, such as RNA- or DNA-containing complexes, could themselves be immunogenic and anti-nucleic acid antibodies could therefore arise (Lotz et al., 1992; Mohan et al., 1993). Such DNA or RNA released from, e.g., apoptotic cells or DNA- or RNA-containing microbes present in serum of autoimmune patients, could be responsible for inflammation that contributes to the autoimmune disease (Fatenejad, 1994; Malmegrim et al., 2002; Newkirk et al., 2001). Indeed CpG-containing sequences could be identified from SLE serum that induces an efficient immune response dominated by IFN-α. secretion that is thought to contribute the development of to autoimmune diseases (Magnusson et al., 2001; Ronnblom et al., 2001). In addition, the epitopes for anti-RNA antibodies could be identified and are composed of G,U-rich sequences (Tsai et al., 1992; Tsai et al., 1993). G,U-rich sequences appear to be natural ligands for TLR7 and TLR8 and, therefore, can mediate immune stimulatory responses that in principle could contribute to autoimmune diseases or the development of autoimmune diseases (PCT/US03/10406).

Specific antigens to which auto-antibodies are produced include β2-glycoprotein, cardiolipin, CCP, CENP, GBM, gliadin, Jo-1, LKM1, La, MPO, Parietal Cell antigens, PR3, Ro, SS-B/La, SS-A/Ro, Scl-70, Sm, sperm transglutaminase, TPO and U1RNP.

Infectious Agents. Infections refer to any condition in which there is an abnormal collection or population of viable intracellular or extracellular microbes in a subject. Various types of microbes can cause infection, including microbes that are bacteria, microbes that are viruses, microbes that are fungi, and microbes that are parasites. Detection of antigens or nucleic acids associated with these microbes, or antibodies thereto, is contemplated in accordance with the present invention.

Bacteria include, the 83 or more distinct serotypes of pneumococci, streptococci such as *S. pyogenes, S. agalactiae, S. equi, S. canis, S. bovis, S. equinus, S. anginosus, S. sanguis, S. salivarius, S. mitis, S. mutans*, other *viridans streptococci, peptostreptococci*, other related species of *streptococci, enterococci* such as *Enterococcus faecalis, Enterococcus faecium, staphylococci*, such as *Staphylococ-* cus epidermidis, Staphylococcus aureus, Hemophilus influenzae, pseudomonas species such as Pseudomonas aeruginosa, Pseudomonas pseudomallei, Pseudomonas mallei, brucellas such as Brucella melitensis, Brucella suis, Brucella abortus, Bordetella pertussis, Borellia species, such as Borellia burgedorferi Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi, etc. Listeria monocytogenes, Nocordia asteroides, Bacteroides species, Actinomycetes species, Treponema pallidum, Leptospirosa species, Haemophilus species, Helicobacter species, including Helicobacter pylori, Treponema species and related organisms. The invention may also be useful against gram negative bacteria such as Klebsiella pneumoniae, Escherichia coli, Proteus, Serratia species, Acinetobacter, Yersinia pestis, Francisella tularensis, Enterobacter species, Bacteriodes and Legionella species, Shigella species, Mycobacterium species (e.g., Mycobacterium tuberculosis, Mycobacterium bovis or other mycobacteria infections), Mycobacterium avium complex (MAC), Mycobacterium marinum, Mycobacterium fortuitum, Mycobacterium kansaii, Yersinia infections (e.g., Yersinia pestis, Yersinia enterocolitica or Yersinia pseudotuberculosis) and the like.

In addition, the invention contemplates detection of parastic organisms such as Cryptosporidium, Entamoeba, Plasmodium spp., such as Plasmodium falciparum, Plasmodium malariae, Plasmodium ovale, and Plasmodium vivax and Toxoplasma gondii, Giardia, Leishmania, Trypanasoma, Trichomonas, Naegleria, Isospora belli, Trichomonas vaginalis, Wunchereria, Ascaris, Schistosoma species, Cyclospora species, for example, and for Chlamydia trachomatis and other Chlamydia infections such as Chlamydia psittaci, or Chlamydia pneumoniae, for example. Of course it is understood that the invention may be used on any pathogen against which an effective antibody can be made.

Fungal and other mycotic pathogens (some of which are described in Human Mycoses (1979; Opportunistic Mycoses of Man and Other Animals (1989); and Scrip's Antifungal Report (1992), are also contemplated as a target of diagnosis. Fungi disease contemplated in the context of the invention include, but are not limited to, Aspergillosis, Black piedra, Candidiasis, Chromomycosis, Cryptococcosis, Onychomycosis, or Otitis externa (otomycosis), Phaeohyphomycosis, Phycomycosis, Pityriasis versicolor, ringworm, Tinea barbae, Tinea capitis, Tinea corporis, Tinea cruris, Tinea favosa, Tinea imbricata, Tinea manuum, Tinea nigra (palmaris), Tinea pedis, Tinea unguium, Torulopsosis, Trichomycosis axillaris, White piedra, and their synonyms, to severe systemic or opportunistic infections, such as, but not limited to, Actinomycosis, Aspergillosis, Candidiasis, Chromomycosis, Coccidioidomycosis, Cryptococcosis, Entomophthoramycosis, Geotrichosis, Histoplasmosis, Mucormycosis, Mycetoma, Nocardiosis, North American Blastomycosis, Paracoccidioidomycosis, Phaeohyphomycosis, Phycomycosis, pneumocystic pneumonia, Pythiosis, Sporotrichosis, and Torulopsosis, and their synonyms, some of which may be fatal. Known fungal and mycotic pathogens include, but are not limited to, Absidia spp., Actinomadura madurae, Actinomyces spp., Allescheria boydii, Alternaria spp., Anthopsis deltoidea, Apophysomyces elegans, Arnium leoporinum, Aspergillus spp., Aureobasidium pullulans, Basidiobolus ranarum, Bipolaris spp., Blastomyces dermatitidis, Candida spp., Cephalosporium spp., Chaetoconidium spp., Chaetomium spp., Cladosporium spp., Coccidioides immitis, Conidiobolus spp., Corynebacterium tenuis, Cryptococcus spp., Cunninghamella bertholletiae, Curvularia spp., Dactylaria spp., Epidermophyton spp., Epidermophyton floccosum, Exserophilum spp., Exophiala spp., Fonsecaea spp., Fusarium spp., Geotrichum spp., Helminthosporium spp., Histoplasma spp., Lecythophora spp., Madurella spp., Malassezia furfur, Microsporum spp., Mucor spp., Mycocentrospora acerina, Nocardia spp., Paracoccidioides brasiliensis, Penicillium spp., Phaeosclera dematioides, Phaeoannellomyces spp., Phialemonium obovatum, Phialophora spp., Phoma spp., Piedraia hortai, Pneumocystis carinii, Pythium insidiosum, Rhinocladiella aquaspersa, Rhizomucor pusillus, Rhizopus spp., Saksenaea vasiformis, Sarcinomyces phaeomuriformis, Sporothrix schenckii, Syncephalastrum racemosum, Taeniolella boppii, Torulopsosis spp., Trichophyton spp., Trichosporon spp., Ulocladium chartarum, Wangiella dermatitidis, Xylohypha spp., Zygomyetes spp. and their synonyms. Other fungi that have pathogenic potential include, but are not limited to, Thermomucor indicae-seudaticae, Radiomyces spp., and other species of known pathogenic genera.

Examples of viruses that have been found in humans include but are not limited to Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); unclassified viruses (e.g., the agent of delta hepatitis (thought to be a defective satellite of hepatitis B virus), Hepatitis C; Norwalk and related viruses, and astroviruses); and resipiratory syncytial virus (RSV).

Other medically relevant microorganisms have been described extensively in the literature, e.g., see Medical Microbiology (1983), the entire contents of which is hereby incorporated by reference.

Cancer antigens. Many human cancers express cell surface molecule that are specific to the cancer cell, i.e., they are not expressed or expressed in greatly reduced quantity by normal human somatic cells. The role of these antigens in cancerogenesis and cancer progression is often poorly understood, however, independent of their biological functions these antigens are attractive antibody targets for diagnostic applications. Such tumor markers include alpha-feto protein, beta-2-microglobulin, bladder tumor antigen, CA 15-3, CA 19-9, CA 72-4, CA-125, calcitonin, carcinoembryonic antigen, epidermal growth factor receptor, estrogen receptor, human chorionic gonadotropin, Her-2/neu, neuron-specific enolase, NPM22, progesterone receptor, prostate specific antigen, prostate-specific membrane antigen, prostatic acid phosphatase, S-100, TA-90 and thyroglobulin.

Toxins, Metals and Chemicals. A particular type of chemical or biological agent is a toxin. Toxins can be biological, i.e., produced by an organism. These include toxins that may be used in biological warfare or terrorism, including ricin, anthrax toxin, and botulism toxin. Other toxins are pesticides (insecticides, herbicides; e.g., organophosphates), industrial contaminants (heavy metals, such as cadmium, thallium, copper, zinc, selenium, antimony, nickel, chromium, arsenic, mercury or lead; complex hydrocarbons, include PCBs, and petroleum byproducts; asbestos), and chemical warfare reagents (sarin, soman, cyclosarin, VX, VG, GV, phosgene oxime, nitrogen mustard, sulfur mustard and cyanogen chloride). Table 1 below shows a further list of toxic industrial chemicals (TICs). A specific list of 12 banned persistant organic pollutants includes PCBs, DDT, dioxins, chlordane, furans, hexochlorobenzene, aldrin, mirex, dieldrin, toxaphene, endrin, and heptachlor.

TABLE 1

TICs listed by hazard index

| High | Medium | Low |
|---|---|---|
| Ammonia (CAS# 7664-41-7) | Acetone cyanohydrin (CAS# 75-86-5) | Allyl isothiocyanate (CAS# 57-06-7) |
| Arsine (CAS# 7784-42-1) | Acrolein (CAS# 107-02-8) | Arsenic trichloride (CAS# 7784-34-1) |
| Boron trichloride (CAS#10294-34-5) | Acrylonitrile (CAS# 107-13-1) | Bromine (CAS# 7726-95-6) |
| Boron trifluoride (CAS#7637-07-2) | Allyl alcohol (CAS# 107-18-6) | Bromine chloride (CAS# 13863-41-7) |
| Carbon disulfide (CAS# 75-15-0) | Allylamine (CAS# 107-11-9) | Bromine pentafluoride (CAS# 7789-30-2) |
| Chlorine (CAS# 7782-50-5) | Allyl chlorocarbonate (CAS# 2937-50-0) | Bromine trifluoride (CAS# 7787-71-5) |
| Diborane (CAS# 19287-45-7) | Boron tribromide (CAS# 10294-33-4) | Carbonyl fluoride (CAS# 353-50-4) |
| Ethylene oxide (CAS# 75-21-8) | Carbon monoxide (CAS# 630-08-0) | Chlorine pentafluoride (CAS# 13637-63-3) |
| Fluorine (CAS# 7782-41-4) | Carbonyl sulfide (CAS# 463-58-1) | Chlorine trifluoride (CAS# 7790-91-2) |
| Formaldehyde (CAS# 50-00-0) | Chloroacetone (CAS# 78-95-5) | Chloroacetaldehyde (CAS# 107-20-0) |
| Hydrogen bromide (CAS# 10035-10-6) | Chloroacetonitrile (CAS# 7790-94-5) | Chloroacetyl chloride (CAS# 79-04-9) |
| Hydrogen chloride (CAS# 7647-01-0) | Chlorosulfonic acid (CAS# 7790-94-5) | Crotonaldehyde (CAS# 123-73-9) |
| Hydrogen cyanide (CAS#74-90-8) | Diketene (CAS# 674-82-8) | Cyanogen chloride (CAS# 506-77-4) |
| Hydrogen fluoride (CAS# 7664-39-3) | 1,2-Dimethylhydrazine (CAS# 540-73-8) | Dimethyl sulfate (CAS# 77-78-1) |
| Hydrogen sulfide (CAS# 7783-0604) | Ethylene dibromide (CAS# 106-93-4) | Diphenylmethane-4.4'-diisocyanate (CAS# 101-68-8) |
| Nitric acid, fuming (CAS# 7697-37-2) | Hydrogen selenide (CAS# 7783-07-5) | Ethyl chlroroformate (CAS# 541-41-3) |
| Phosgene (CAS# 75-44-5) | Methanesulfonyl chloride (CAS# 124-63-0) | Ethyl chlorothioformate (CAS# 2941-64-2) |
| Phosphorus trichloride (CAS# 7719-12-2) | Methyl bromide (CAS# 74-83-9) | Ethyl phosphonothioic dichloride (CAS# 993-43-1) |
| Sulfur dioxide (CAS# 7446-09-5) | Methyl chloroformate (CAS# 79-22-1) | Ethyl phosphonic dichloride (CAS# 1066-50-8) |
| Sulfuric acid (CAS# 7664-93-9) | Methyl chlorosilane (CAS# 993-00-0) | Ethyleneimine (CAS# 151-56-4) |
| Tungsten hexafluoride (CAS# 7783-82-6) | Methyl hydrazine (CAS# 60-34-4) | Hexachlorocyclopentadiene (CAS# 77-47-4) |
|  | Methyl isocyanate (CAS# 624-83-9) | Hydrogen iodide (CAS# 10034-85-2) |
|  | Methyl mercaptan (CAS# 74-93-1) | Iron pentacarbonyl (CAS# 13463-40-6) |
|  | Nitrogen dioxide (CAS# 10102-44-0) | Isobutyl chloroformate (CAS# 543-27-1) |
|  | Phosphine (CAS# 7803-51-2) | Isopropyl chloroformate (CAS# 108-23-6) |
|  | Phosphorus oxychloride (CAS# 10025-87-3) | Isopropyl isocyanate (CAS# 1795-48-8) |
|  | Phosphorus pentafluoride (CAS# 7647-19-0) | n-Butyl chloroformate (CAS# 592-34-7) |
|  | Selenium hexafluoride (CAS# 7783-79-1) | n-Butyl isocyanate (CAS# 111-36-4) |
|  | Silicon tetrafluoride (CAS# 7783-61-1) | Nitric oxide (CAS# 10102-43-9) |
|  | Stibine (CAS# 7803-52-3) | n-Propyl chloroformate (CAS# 109-61-5) |
|  | Sulfur trioxide (CAS# 7446-11-9) | Parathion (CAS#: 56-38-2) |
|  | Sulfuryl fluoride (CAS# 2699-79-8) | Perchloromethyl mercaptan (CAS# 594-42-3) |
|  | Tellurium hexafluoride (CAS# 7783-80-4) | sec-Butyl chloroformate (CAS# 17462-58-7) |
|  | n-Octyl mercaptan (CAS# 111-88-6) | tert-Butyl isocyanate (CAS# 1609-86-5) |

TABLE 1-continued

TICs listed by hazard index

| High | Medium | Low |
|---|---|---|
| | Titanium tetrachloride (CAS# 7550-45-0) | Tetraethyl lead (CAS# 78-00-2) |
| | Tricholoroacetyl chloride (CAS# 76-02-8) | Tetraethyl pyrophosphate (CAS# 107-49-3) |
| | Trifluoroacetyl chloride (CAS# 354-32-5) | Tetramethyl lead (CAS# 75-74-1) |
| | | Toluene 2.4-diisocyanate (CAS# 584-84-9) |
| | | Toluene 2.6-diisocyanate (CAS# 91-08-7) |

Plant products. In certain embodiments, the present invention will allow one to assess the content of plant materials. For example, one can measure the health of a plant by measuring the nutrient content of the plants' leaves. One can also make decisions about harvesting of crops by assessing the content of fruit or vegetable tissue. For example, in wine-making, the sugar content of grapes is an important factor in determining harvest time. Also, when selecting crops for breeding, identifying plants with various desirable traits (nutrient content, expression of endogenous products or transgenes) is critical.

Drugs. In another aspect of the invention, the assays maybe used to detect or measure drugs in samples. The drugs may be therapeutic agents, and the assay is designed to assess drug levels in the subject with the goal of optimizing dosage. Alternatively, illicit drugs may be detected, and include alcohol, amphetamines, methamphetamine, MDMA, barbiturates, phenobarbitol, benzodiazepines, *cannabis*, cocaine, codeine, morphine, cotinine, heroin, LSD, methadone, PCP, or licit drugs banned for particular purposes, such as sporting events, including anabolic steroids, hormones (EPO, hGH, IGF-1, hCG, insulin, corticotrophins). β2 agonists, anti-estrogens, diuretics, stimulants, and glucocorticosteroids.

Lipids. Lipids are biologically relevant targets for assays of the present invention. For example, the ability to detect and quantitate lipids in the blood can serve to assess risk of atherosclerotic disease, as well as to monitor the efficacy of therapy therefore. Thus, LDL, HDL and triglyceride measurements are of use.

Sugars. While assessing sugar levels may be of general medical interest, sugars are particularly relevant to diabetes management and therapy. Other sugars of relevance include those produced by bacteria and fungi in biofilm formation, and those produced during food or beverage production.

V. Kits

In accordance with the present invention, various reagents may be packaged in the form of a kit. The kit may comprise a suitably aliquoted particles/beads in derivatized or underivatized form, and may also include reagents for derivatization, wash solutions, blocking agents, reporter molecules, means for detecting the reporter molecule, a suitable flat, non-permeable surface, and one or more binding agents.

The components of the kits may be packaged either in aqueous media or in lyophilized form. When reagents and/or components are provided as a dry powder, the powder can be reconstituted by the addition of a suitable solvent. It is envisioned that the solvent may also be provided. Additionally, a surface with a particle/bead pre-bound thereto also may be provided.

The container means of the kits will generally include at least one vial, test tube, flask, bottle, syringe or other container means, into which a component may be placed, and preferably, suitably aliquoted. Where there is more than one component in the kit, the kit also will generally contain a second, third or other additional containers into which the additional components may be separately placed. However, various combinations of components may be comprised in a vial. The kits of the present invention also will typically include a means for containing the reagent vials and other kit components in close confinement for commercial sale. Such containers may include injection or blow molded plastic containers into which the desired vials are retained.

Irrespective of the number or type of containers, the kits of the invention may also comprise, or be packaged with, instructions for use of the various reagents.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Figure 4:
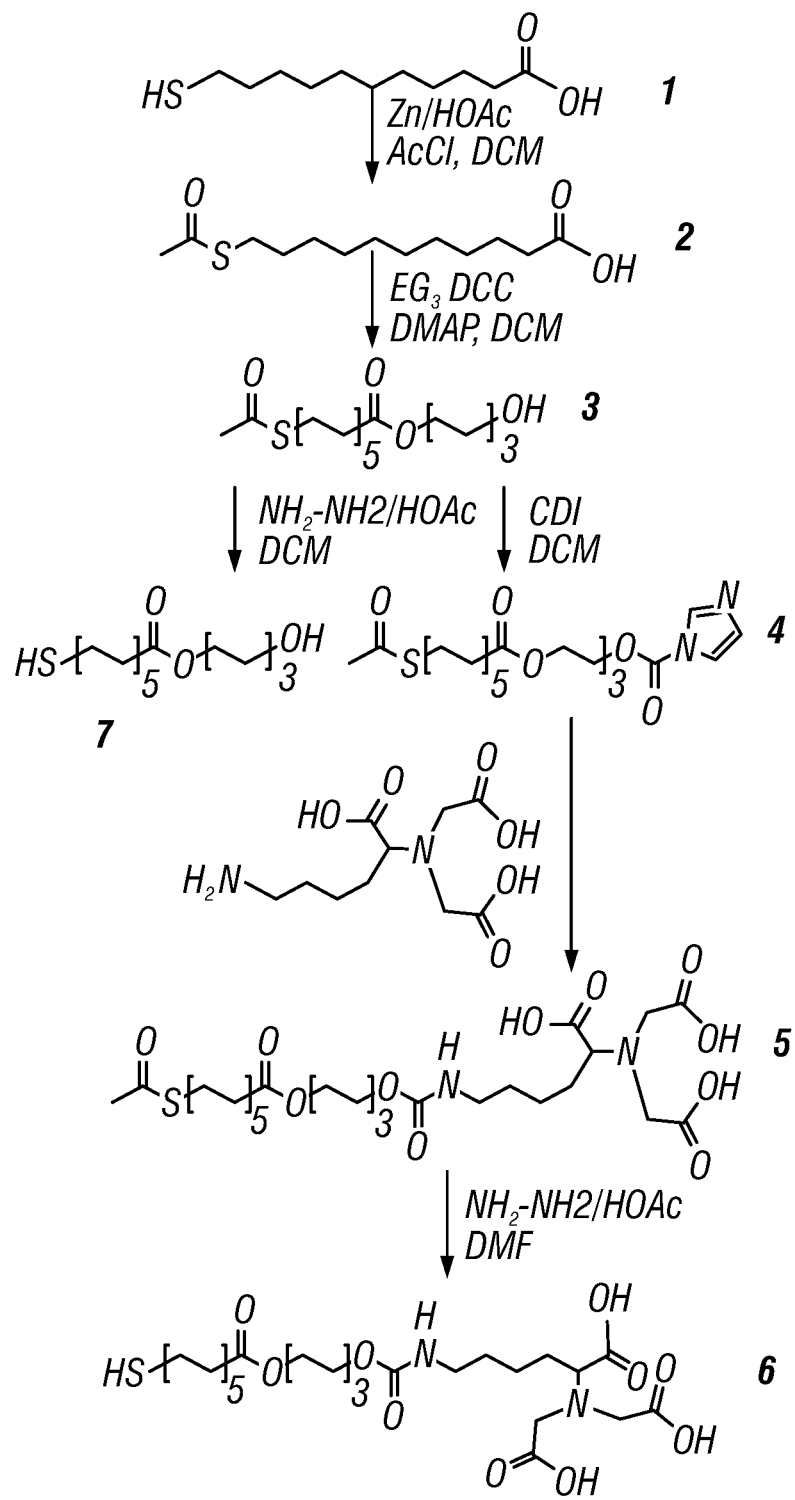
FIG. 4—Synthetic route for the NTA ligand and spacer ligand.

Synthesis of Ni-NTA Gold Nanoparticles. The synthesis of NTA ligand was based on two previous studies that conjugated an alkane thiol to a lysine modified NTA ligand through a triethylene glycol spacer (FIG. 4) (Tinazli et al., 2005; Schmitt et al., 2000). In this study, 11-mercaptoundecanoic acid (11-MUA) was coupled to a triethylene glycol moiety. Ethylene glycol serves to improve solubility of the nanoparticle, as well as minimize non-specific protein binding (Schmitt et al., 2000; Mrksich et al., 1996; Palegrosdemange et al., 1991; Prime & Whiteside, 1991; Sigal et al., 1996). The thiol group in 11-MUA (1) was first protected by acetylation using zinc acetate to yield 11-acetyl-sulfanyl-undecanoic acid (2). This intermediate was coupled to the triethylene glycol moiety through an ester bond to afford S-acetyl-MUA-PEG-OH (3). Activation of (3) with carbonyl-diimidazole (CDI) creates a stable imidazoloid adduct (4) that can be purified by silica chromatography. Reacting (4) with Nα,Nα-Methylcarboxy-L-lysine under basic conditions resulted in carbamate formation, which can be extracted with ethyl acetate after adjusting the pH to 1.5.

Finally, the sulfur of (5) was deprotected using hydrazine acetate under nitrogen and purified by size-exclusion chromatography to afford the final NTA-thiol ligand (6).

Figure 5:
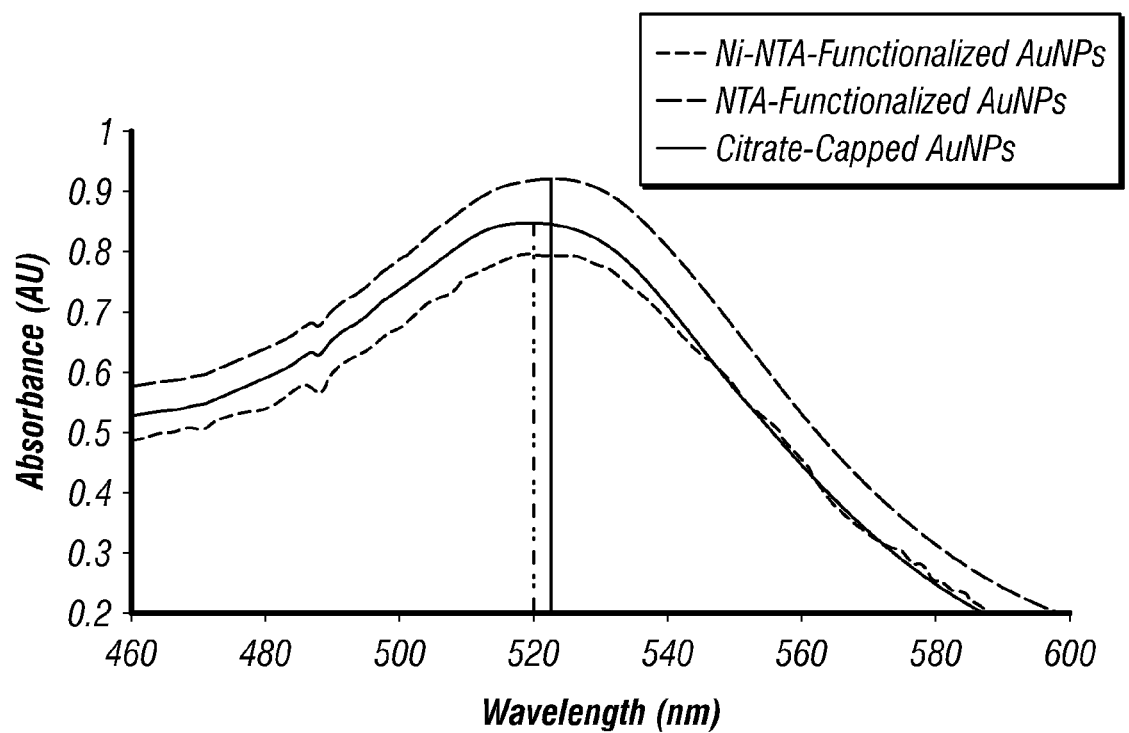
FIG. 5—Plasmon absorption spectra of a stock solution of citrate-stabilized (blue), NTA-functionalized (purple), and Ni-NTA-functionalized AuNPs (light blue).

Addition of the NTA ligand (6) to 15 nm citrate-stabilized gold nanoparticles was achieved by overnight ligand exchange by adding the ligand to the AuNPs in water. A charge-stabilized self-assembled monolayer of the NTA ligand was created on the AuNPs, altering the refractive index and hydrodynamic radius of the particle. The reaction was monitored by UV-Visible spectrometry, which revealed a Plasmon resonance shift of 3 nm (FIG. 5). Dynamic light scattering (DLS) measurements confirmed a 3 nm increase in particle diameter (19.9±0.7 nm to 22.8±0.2 nm) caused by a change in the hydrodynamic radius of the ligand-containing AuNPs. After washing and removing the excess ligand through centrifugation, the NTA-AuNP was charged with $Ni^{2+}$ for 30 minutes. The particles were washed three times, resuspended in buffer, and characterized using UV-Vis and DLS (FIG. 5). Particle diameters were identical to those observed for the NTA AuNPs.

Figure 6:
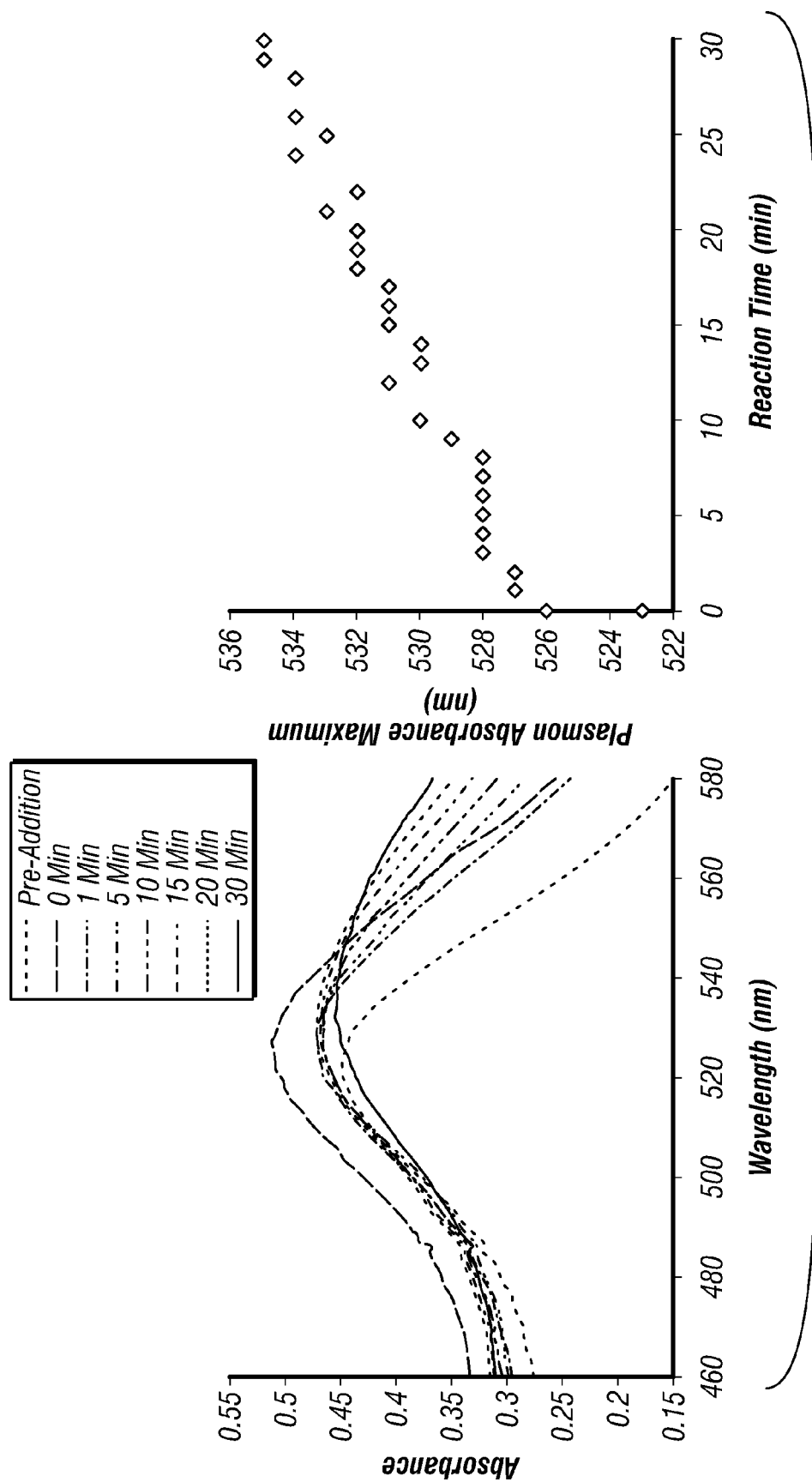
FIG. 6—Time study of PLH addition to Ni-NTA AuNPs. Left: UV-Visible Plasmon absorption spectrum as a function of time. Right: Trend of increasing Plasmon absorbance maximum as a function of time. Note: The pre-addition and 0 min values are denoted at 0 min.

To understand the behavior of the Ni-NTA AuNP-target interaction, 100 µL of Ni-NTA AuNPs ($1.4\times10^{12}$ particles/mL) were incubated with a 10 µL solution of 0.2 mg/mL PLH and monitored over time by UV-Vis (FIG. 6). Upon addition of PLH, an immediate red shift of 3 nm occurs, and continued to shift throughout the duration of the experiment. During the initial addition of the target, the overall absorbance of the Plasmon resonance band increases. It may be possibly due to turbidity caused by the initial mixing of the solution or induced by a surface interaction between the target and the Ni-NTA ligand on the particle. It should be noted that after the 30 minute time point, visible aggregation can be observed in the solution.

Figure 7A:
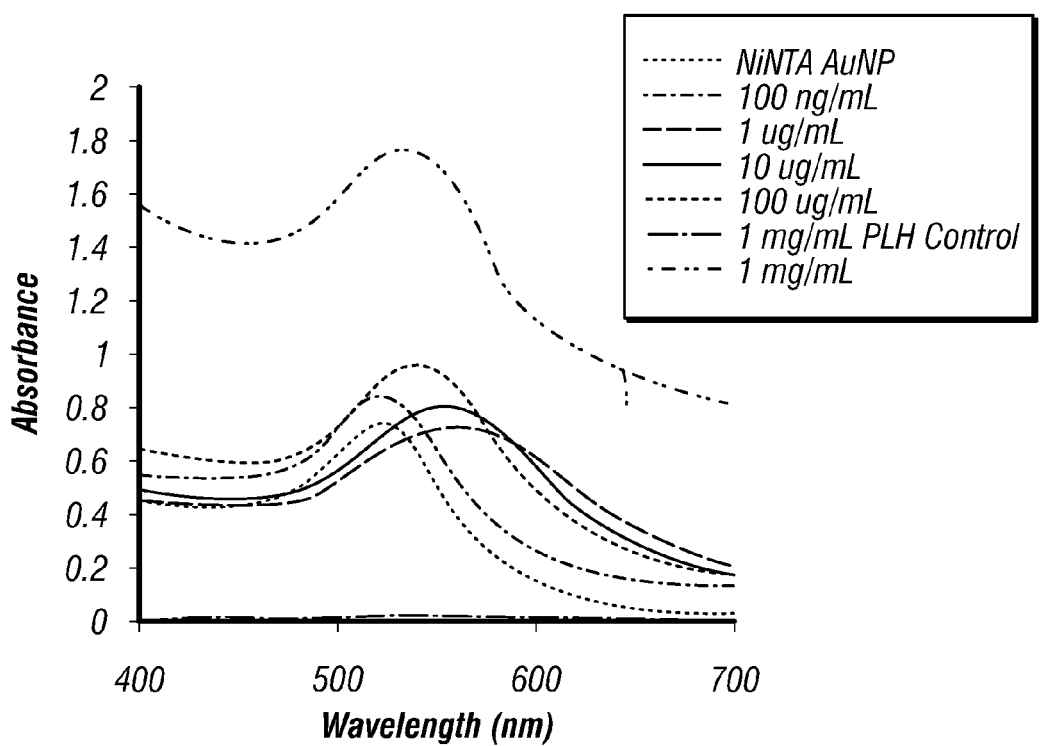
FIGS. 7A-B—(FIG. 7A) UV-Visible spectrum of PLH titrations with Ni-NTA AuNPs.
Figure 7B:
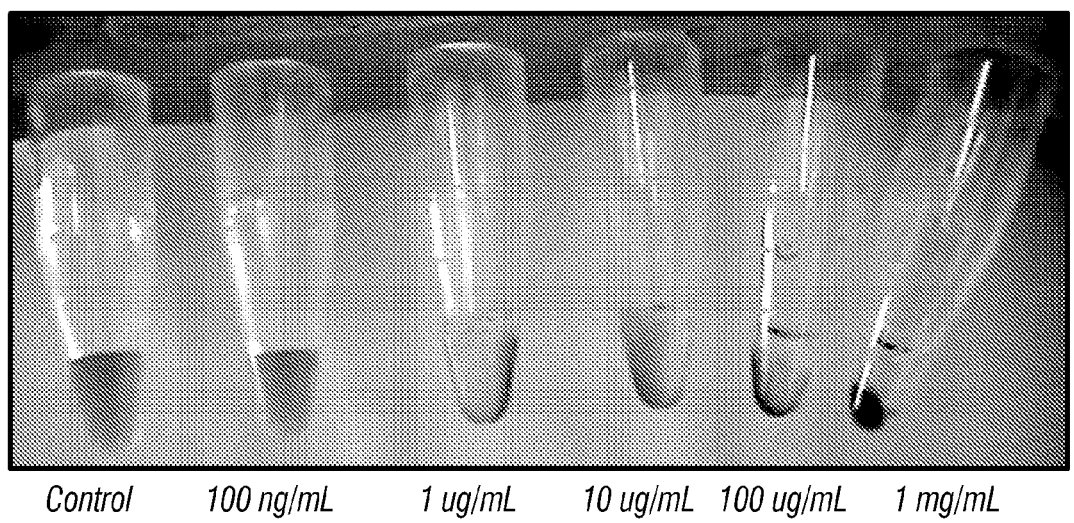

Next, to determine the behavior of the Ni-NTA AuNPs in the presence of the target, a series of PLH concentrations were tested by incubating 90 µL of AuNPs with 10 µL of PLH. The reaction was allowed to proceed for 15 minutes and UV-Vis measurements were taken. At 1 mg/mL, the solution initially turned a bright pink color before aggregating prior to the 15 minutes of incubation. The aggregation led to the drastic increase of absorbance (FIGS. 7A-B). At 100 µg/mL, the solution initially turned more purple than the 1 mg/mL sample before visible aggregation was observed. This aggregation was not observed in the 15 minute time frame, but was clearly seen from the images after overnight incubation of the samples (FIGS. 7A-B). As the PLH concentration was decreased to 10 µg/mL and 1 µg/mL, a purple solution was observed, indicative of aggregation of the AuNPs. The lowest concentration (100 ng/mL) did not show a significant change in color, however a Plasmon resonance shift of 3 nm was observed.

The working hypothesis is that the interactions between the AuNPs and the target are concentration dependant. At the lowest concentrations of target, the AuNP concentration is higher, meaning that multiple AuNPs should be available to interact with a single target molecule. As a result, multiple particles are localized, resulting in a red shift in their Plasmon absorbance. As the target concentration is increased, it begins to coat the AuNPs such that a single target may conjugate to fewer AuNPs, resulting in a less profound red shift. The aggregation in this case would then be caused by protein-protein interactions of the PLH rather than crosslinking of the AuNPs by a single target. Currently, the inventors are conducting TEM analysis to elucidate the aggregate size and morphology under these conditions.

Figure 8:
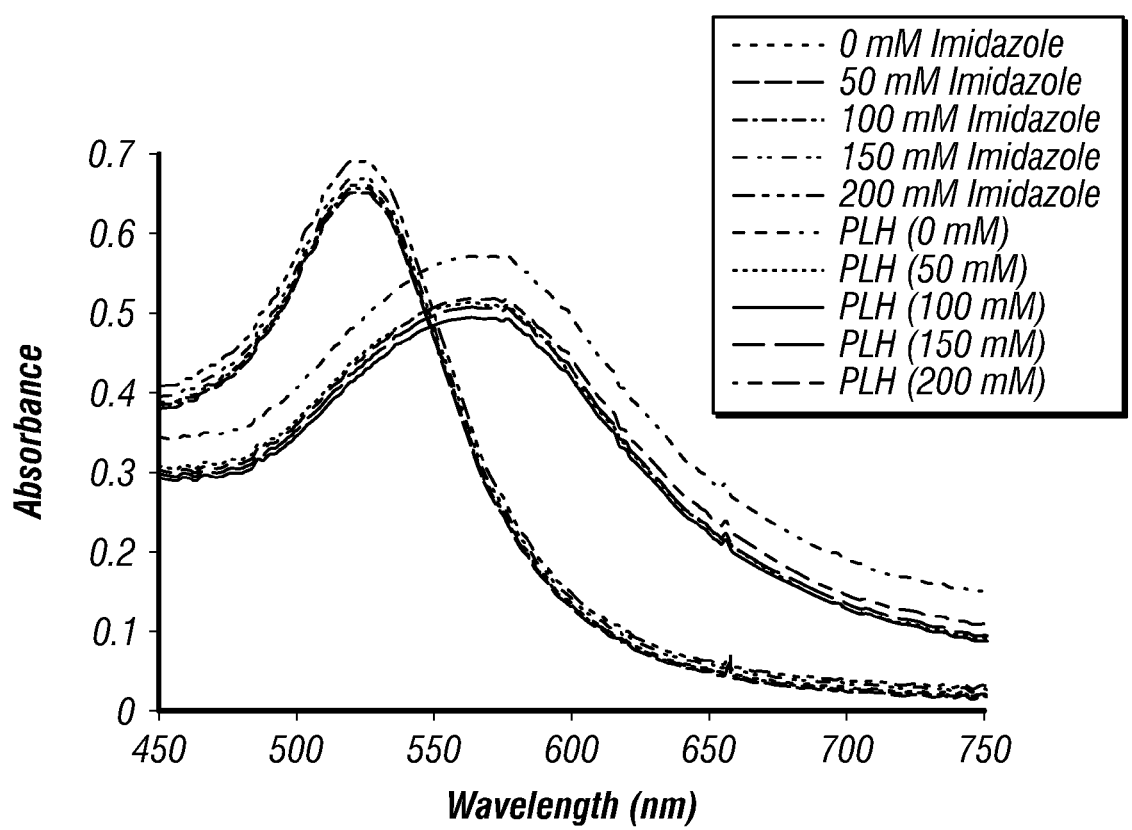
FIG. 8—Effect of imidazole on PLH-induced aggregated of Ni-NTA AuNPs. No major change was observed when imidazole was added to the AuNPs (left), but aggregation readily occurs when 1 µg/mL PLH is added (right).

The selectivity of the diagnostic is predicated on the fact that pfHRP2 has a higher binding affinity to Ni-NTA than any other compound that will be found in a patient sample, including albumen and histidine rich glycoprotein. A low concentration of imidazole (<200 mM) should minimize non-specific interactions between the AuNPs and other proteins found in a patient sample by competing for available Ni-NTA sites, while not significantly affecting the target-Ni-NTA interaction (Panton et al., 1989). It is unknown, however whether imidazole will destabilize the AuNPs and induce aggregation. To examine this, a 10 µL solution of imidazole was added to 90 µL of Ni-NTA AuNPs and incubated for 15 minutes before being monitored by UV-Vis spectroscopy (FIG. 8). The Ni-NTA AuNPs showed little change in their Plasmon absorbance after imidazole addition. When imidazole was added to citrate-stabilized AuNPs and NTA AuNPs without Ni(II), the particles immediately aggregated (data not shown), suggesting that the $Ni^{2+}$ serves to stabilize the particles by binding to both the carboxylic acids on the NTA ligand and the imidazole in solution. Without the counter ion, the imidazole interacts with the acidic ligand, thus destabilizing the nanoparticle. It should be noted that although imidazole is a base, the pH was maintained at 7.4 during these experiments. If the pH would have been raised by the addition of imidazole, then it could be argued that the destabilization was caused by a change in pH rather than the addition of imidazole. Next, a 10 µL solution of PLH (1 µg/mL final concentration) was added to the particles and incubated for 30 minutes. All of the samples showed a significant Plasmon resonance shift (523 nm to 660 nm), suggesting that significant aggregation occurred (FIG. 8). By visual inspection, a clear color change from red to purple occurred within seconds after the addition of the PLH. This suggests that even at high concentrations of imidazole, PLH still has the same aggregation effect. This implies that the sensitivity of the assay is not affected by the non-specific blocking agent.

EXAMPLE 2

Figure 1:
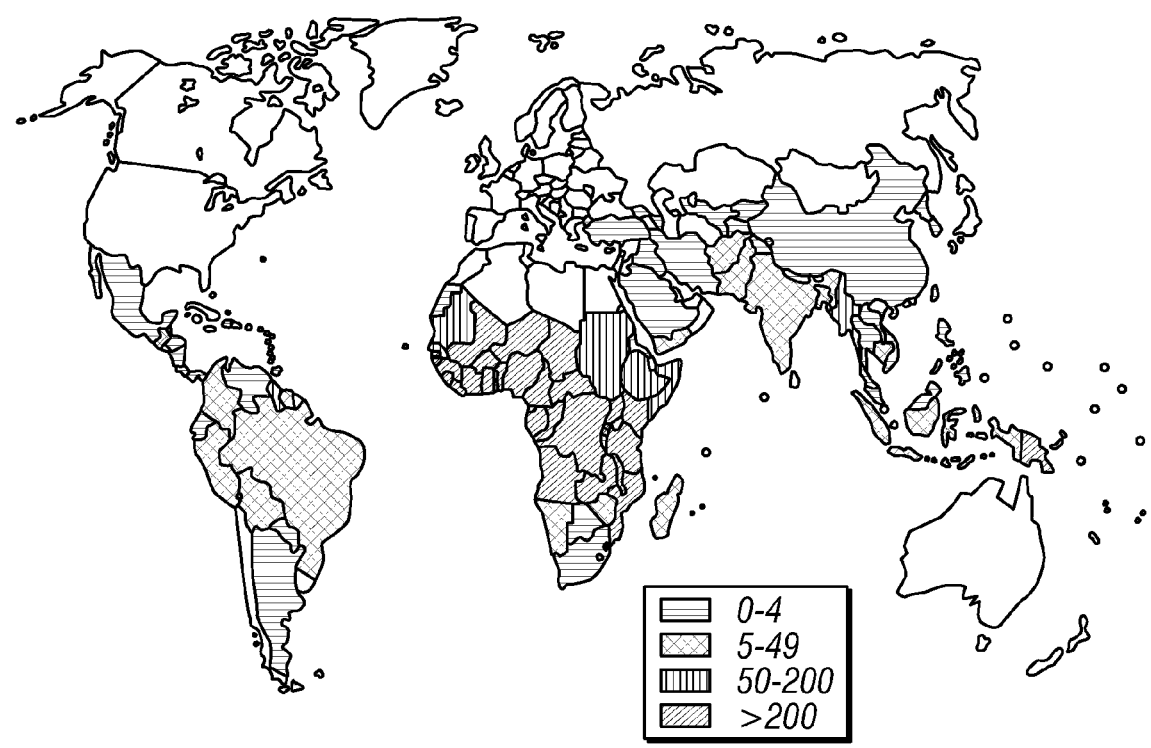
FIG. 1—Estimated incidence of malaria per 100 population, 2006 (WHO, 2006).
Figure 2:
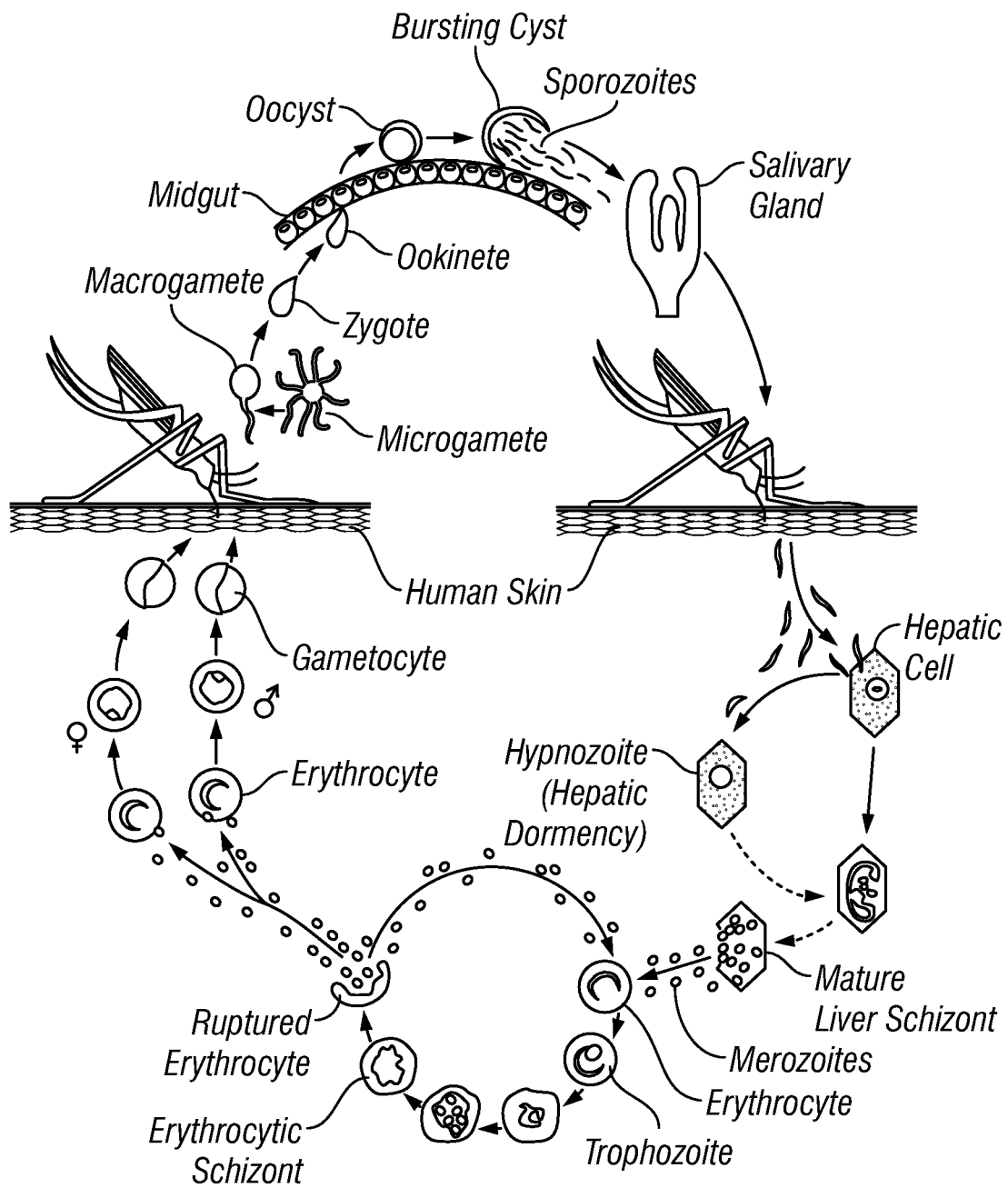
FIG. 2—Life cycle of the malarial parasite (Weissbuch & Leiserowitz, 2008).
Figure 3:
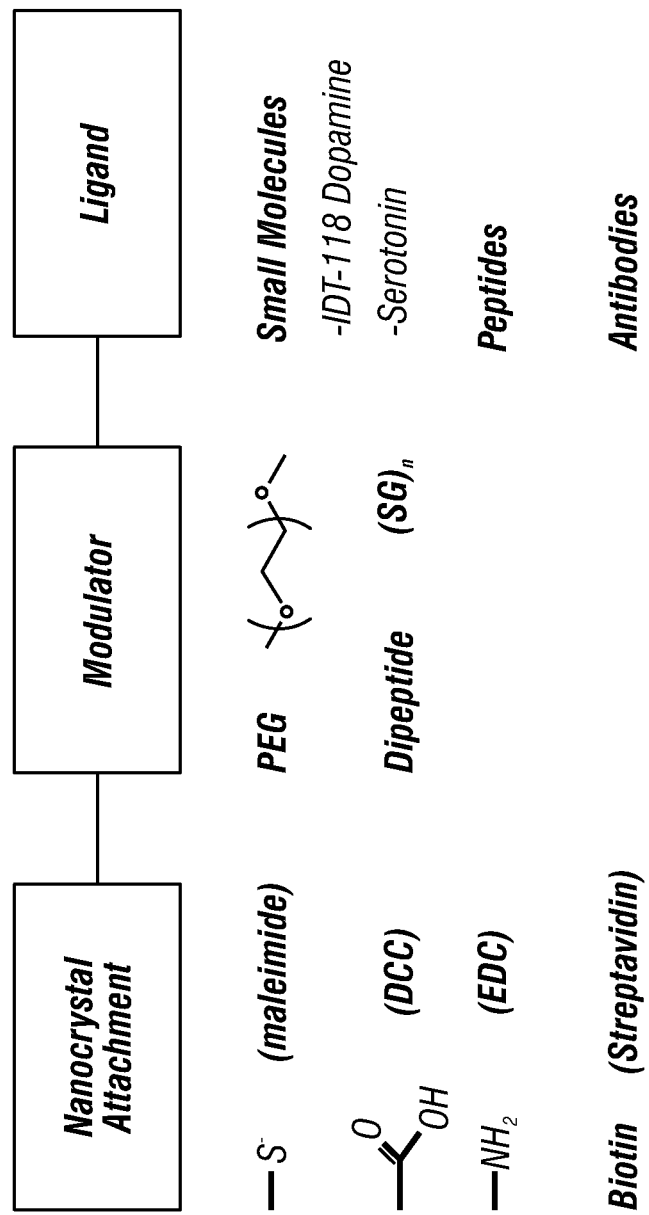
FIG. 3—Modular Ligand Design Strategy.

The surface of beads or particles can be decorated with the probe/capture agent using a variety of methodologies. For example, one design uses a modular ligand in which there is a functional moiety to couple to the bead/particle surface (e.g., in the case of the gold nanoparticles this is a thiol), a module to limit non-specific binding (i.e., polyethyleneglycol PEG unit) and then the probe/capture agent (FIG. 3). Another approach would be to make a mixed surface with the probe capture agent and a ligand to limit non-specific binding distributed evenly across the surface.

EXAMPLE 3

Figure 15:
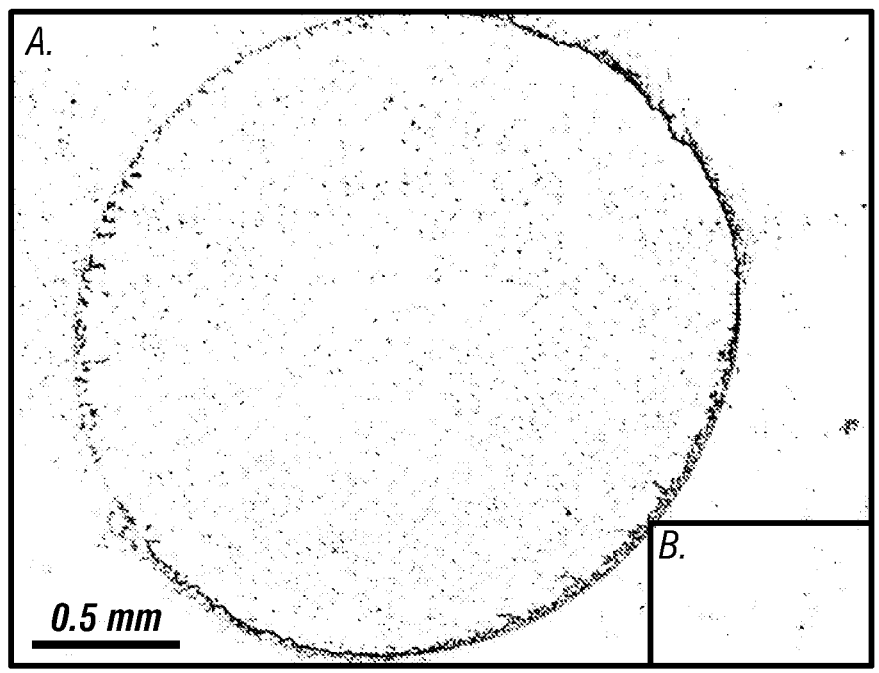
FIGS. 15A-B—Aggregation and ring formation induced by poly-L-histidine target imaged with light microscopy. Ni(II)NTA AuNPs (2 nM, $1.2 \times 10^9$ particles/uL) were incubated with poly-L-histidine for 15 minutes and deposited (1 µL) onto a NiNTA functionalized slide. After a 15 minute incubation period, the slide was washed to remove excess unbound Ni(II)NTA AuNPs.

A single particle assay is shown in FIGS. 15A-B. There, a solution containing 2 nM Ni(II)NTA AuNPs (9 µL) in 0.1 M HEPES pH 7.4 with 0.025% Tween 20 was mixed with a solution containing 1 µL of 100 µg/mL Poly-L-Histidine and incubated at room temperature for 15 minutes. Next, 1 µL of the reaction mixture was deposited onto a Ni(II)NTA glass slide (Xenopore Corp) and dried for 15 minutes. The slide was then washed first by immersing into a solution containing 0.1 M HEPES buffer pH 7.4 with 200 mM imidazole and secondly by immersing into water. The slide was dried by a gentle stream of nitrogen and ring formation was observed using microscopy.

Preparation of necessary diagnostic reagents. The preparation of the diagnostic reagents was divided into two components: the synthesis of the nanoparticle aggregation reagent and the preparation of the capture surface. As detailed below, the inventors have successfully demonstrated the ability to synthesize the necessary diagnostic components from readily available commercial starting materials in high yields with excellent purity, which will ultimately lower the cost.

Figure 16:
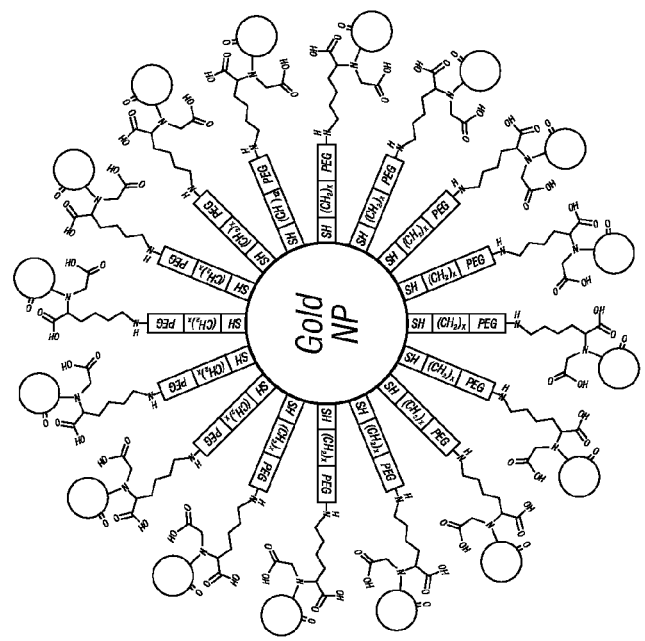
FIG. 16—Synthesis of Ni(II)NTA AuNPs. Ni(II)NTA AuNPs were synthesized by incubating AuNPs with thiolated NTA ligand overnight. After purification, the particles were then charged overnight with Ni(II) and purified.

The strategy for the assembly of the nanoparticle aggregation reagents employs a modular approach (FIG. 16) that affords maximum flexibility in the final format of the diagnostic device. Briefly, the core of the aggregation reagent is a gold (Au) nanoparticle, 15 nm in diameter, decorated with a molecular recognition ligand. This ligand is consists of (1) a module for nanoparticle attachment—the free thiol; (2) a module to minimize non-specific binding—the PEG component; and (3) a target recognition module—a nickel nitrilotriacetic acid (Ni(II)NTA) complex. The advantage to this approach is that one can readily manipulate any of the modules to better respond to assay performance requirements. Synthesis of the molecular recognition ligand utilized readily available starting materials and proceeded in high overall yields of 70%.

Figure 18C:
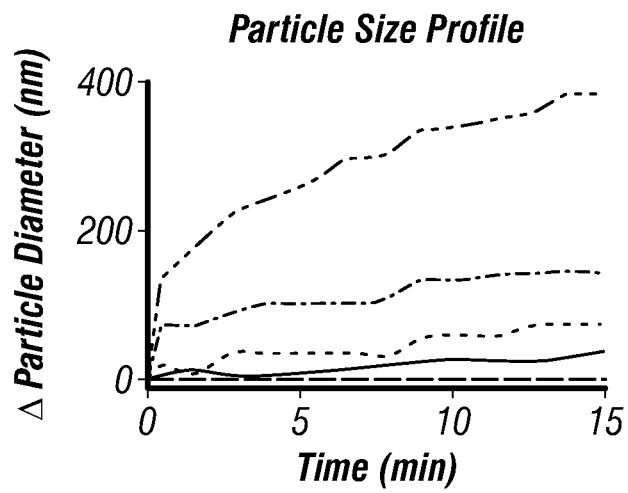

The nanoparticle ligand constructs were produced with nearly 100% efficiency using methods based on literature procedures. Briefly, a solution of commercially available citrate-stabilized AuNPs (15 nm) was incubated with the modular NTA-thiol ligand overnight at room temperature. After the initial loading of ligand, the resulting solution was buffered and the particles subsequently charge-stabilized in a salt solution before purification. The particles were then charged with Ni(II) overnight and purified by additional washes. The resulting nanoparticles were monodisperse as demonstrated by the predicted Plasmon absorption peak at 525 nm and by transmission electron microscopy (TEM) (FIGS. 18A-C).

The second component of the diagnostic reagents is the capture surface (FIG. 17A). The function of the capture surface is to tightly bind the aggregated particle/target to the surface through metal chelation. Tight coupling is necessary for subsequent processing to remove non-binding materials from the device. It is also important to have control over the surface chemistry of the slide in that this allows the tuning of drop geometry and the radial flow characteristics inside the evaporating drop. The surface chemistry can have a dramatic impact on drop geometry and ring formation as shown in FIG. 17B. For each slide, a similar volume of analyte was spotted. The most evident ring formation occurred for those surfaces with contact angles less than 20 degrees (i.e., the uncoated and PEG coated surfaces). This suggests that the ultimate capture surface design will need a formatted surface that will optimize the desired drop geometry for ring formation.

The slides were prepared using a modular approach similar to that employed in the design of the nanoparticle ligand above. The slide surface was functionalized to create a monolayer of amines by reacting a solution of 3-aminopropyltriethoxysilane (APTES) with the glass slide overnight. The resulting surface amines were activated by reaction with gluteraldehyde and cross-linked to N-bis-carboxymethyl-L-lysine hydrate (NTA). The resulting chelates were then charged with Ni(II) overnight, rinsed and dried for storage. The resulting surfaces were used to demonstrate target capture (FIG. 17C). Ni(II)NTA slides were spotted with a range of surrogate target (the polymer poly-L-Histidine, PLH) concentrations. The slides were rinsed and then dipped into a solution of Au—Ni(II)NTA nanoparticles, and rinsed again. The purple spots highlight the regions of the capture slide upon which the Au particles aggregated due to the presence of target which had specifically bound to the Ni(II)NTA moiety on the slide surface.

A final but important component that has been developed was to establish cultures of $P.\ falciparum$. Maintenance of these cultures provides us with a readily available stock of HRP II for further studies. Additionally, the inventors have published on the synthesis of HRP II peptide analogs and mimics. This has provided the inventors us with a readily available source of a surrogate target.

Figure 19:
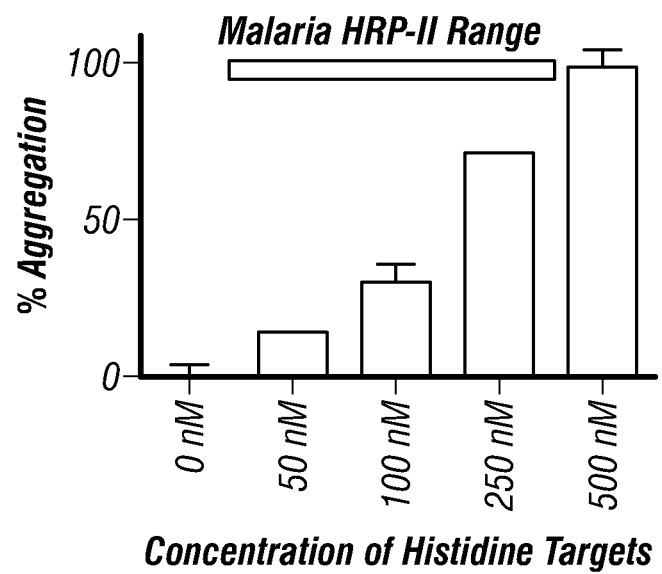
FIG. 19—Aggregation profile of Ni(II)NTA AuNPs in the presence of PLH. Aggregation of the particles with PLH is observed within the predicted concentration range of pfHRP-II found in patients with a parasite load of 200-5000 parasites/pt.
Figure 21:
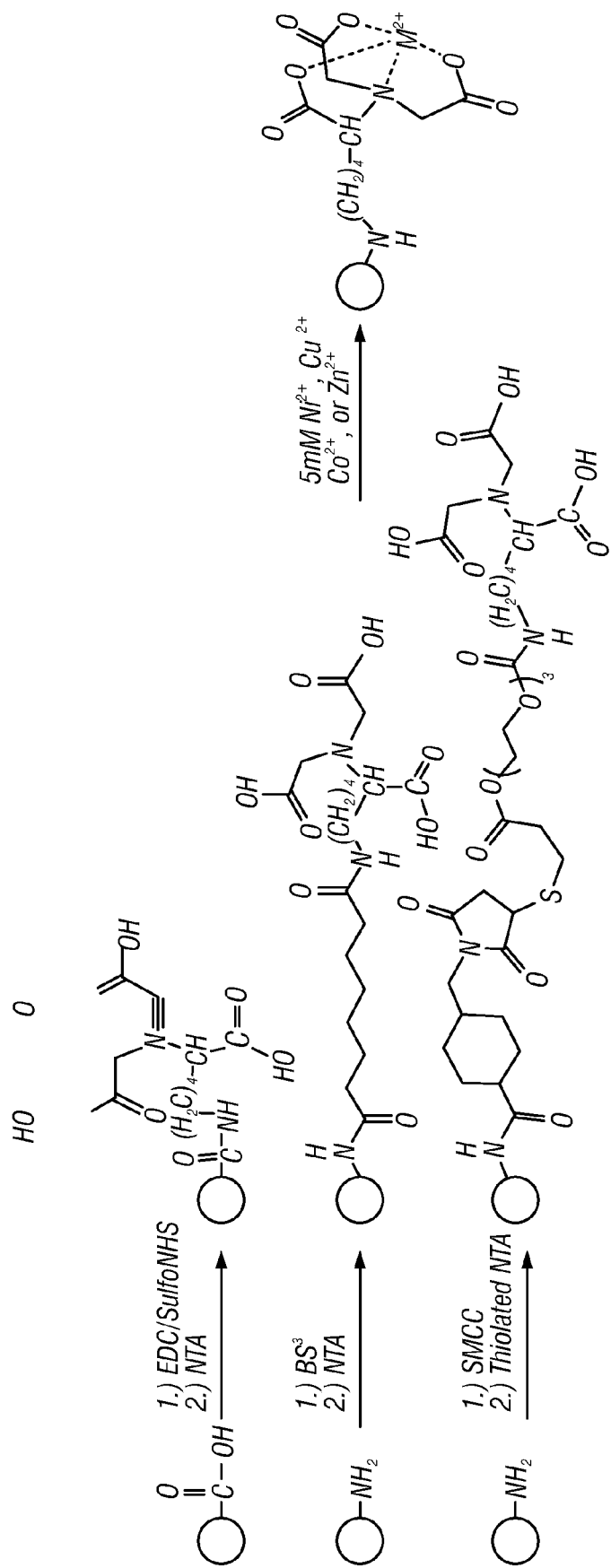
FIG. 21—Coupling strategies for surface functionalization of particles.

Optimized conditions for detection of HRP II. The detectable color change of the proposed diagnostic in Phase I was designed to take advantage of the dramatic color change observed as the red of the monodisperse particles shifts to the blue/purple characteristic of aggregated clusters (FIG. 18A). This transition is enabled through the cross-linking of histidine sites within the HRP II protein and the Ni(II)NTA component of the nanoparticle ligand. When the surrogate target PLH is titrated against a stock concentration of Ni(II)NTA Au nanoparticles, the absorption spectrum shifts dramatically to a higher wavelength (FIG. 18B), characteristic of aggregated Au nanoparticles. Aggregation was also observable using dynamic light scattering measurements (FIG. 18C). At high target concentrations (500 nM), aggregates of 400 nm in diameter were achieved in 15 minutes, while at the low end of the range (50 nM), aggregates of approximately 40 nm in diameter were formed. These experiments demonstrate that the aggregation step of the assay will take approximately 15 minutes to reach completion. The aggregation of the particles was confirmed by transmission electron microscopy (FIG. 18A). Once the reaction times were optimized, a solution of Ni(II)NTA functionalized Au particles was titrated with decreasing concentrations of surrogate target to determine the limit of detection (FIG. 19). Spectrophotometrically, the limit of detection of the Au aggregation component of the assay was 50 nM histidine equivalent target; well within the physiological range of HRP II histidine targets reported to be between a lower limit of 1-70 nM and an upper limit of 250-500 nM).

Aggregate capture is possible in simple aqueous solutions (FIGS. 15A-B) producing the predicted purple ring. However, initial efforts to bind more complex solutions (i.e., better mimics of actual testing conditions) of aggregated gold nanoparticles to commercially available uniformly coated capture surfaces have only been marginally successful. One problem is the use of the uniformly coated slide, in that it presents capture sites across the entire surface as the aggregated particles flow to the pin lines. This results in some snagging of aggregated particles as they flow along the surface on their way to the edge. Consequently, uniform capture surfaces produce disks of deposited materials rather than the desired rings, resulting in a loss of visual contrast that is essential for the user interface of the device (compare FIG. 17B panels ii & iv and panels i & iii).

Determination of the sensitivity and specificity of the assay in an increasingly complex biological matrix. The World Health Organization (WHO) has established benchmarks for rapid diagnostic tests (RDT) for malaria. At the lower limit of detection, WHO has identified performance criteria for RDTs with a lower limit of detection of 200 parasites/μl with a dynamic range up to 2000-5000 parasites/μl. Using reported literature values for the secretion of HRP II at these two parasitemias, one may extrapolate HRP II concentrations of 1-70 nM as the lower limit and 250-500 nM concentration at the high range. Under the simplest conditions (phosphate buffered saline), the spectrophotometrically demonstrated limit of detection for the aggregation reagents are within the WHO benchmark for 200 parasites/ul. During the Phase I studies, as the biological matrix became increasingly complex and surrogate target was dissolved in saliva or blood, there was a loss of sensitivity. In the current implementation, this pushed the assay limit of detection beyond the upper limits of the WHO benchmark by two-fold. One explanation for this shift of sensitivity is that unknown proteins within the relevant biological samples bind the nanoparticles, essentially rendering them incapable of participating in aggregation. Consequently, there would not be enough particles to effectively aggregate the HRP II.

A histidine-rich glycoprotein was identified as a known host reagent that might compete with HRP II for aggregation reagents. When Ni(II)NTA Au particles were reacted with isolated HRG over a broad concentration range, there was only a slight loss of absorbance and no detectable shift (FIG. 20A). Furthermore, DLS experiments showed that there was no increase in particle size, suggesting that HRG did not induce aggregation. Since HRG was not the culprit, attention turned to those proteins that exist in high concentrations in blood or serum such as serum albumin. Reaction of Ni(II) NTA Au particles with serum albumin over a wide range of concentrations showed little perturbation of the absorption spectra (FIG. 20B). Similarly, DLS revealed no indication of protein induced aggregation, making serum albumin an unlikely cause of the loss of sensitivity. Having eliminated the most likely competitor for Ni(II)NTA binding and one of the most prevalent proteins in the sample matrix, an experiment analogous to an "affinity pulldown" or immunoprecipitation was performed in which the particles were incubated in serum for 15 minutes and then isolated by centrifugation. Adsorbed proteins were eluted and run on an SDS page gel. This suggests that there is an element of non-specific interactions that must be addressed in order to regain the desired assay sensitivity. Preliminary results suggest that several proteins, including alpha$_2$-macroglobulin, hemoglobin and transferrin potentially interact with the aggregation reagent. Proteomic methods will provide more specific identification if needed.

TABLE 2

Properties of Core Particles

| Core | Diameter (nm) | Density (kg/m$^3$) | Settling velocity (m/s) |
|---|---|---|---|
| Au | 15 | 19.30 | $2 \times 10^{-9}$ |
| Si | 100 | 2.10 | $6 \times 10^{-9}$ |
| Si | 300 | 2.10 | $5 \times 10^{-8}$ |
| PS | 1,390 | 1.05 | $5 \times 10^{-8}$ |

Figure 23:
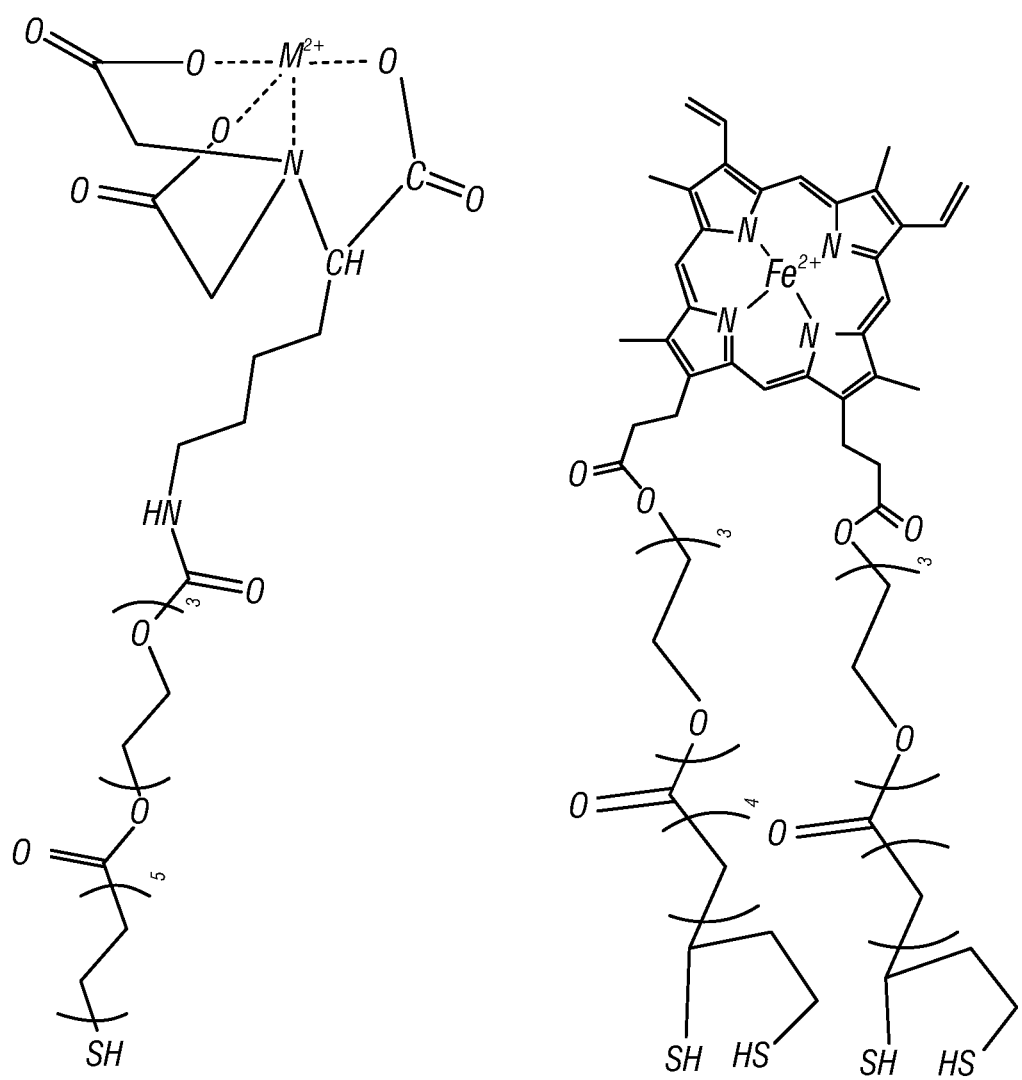
FIG. 23—Modular aspects of proposed capture ligands.

Improved core particles. Given the challenges of observing low numbers of small Au nanoparticles, one obvious approach would be to increase their size. Unfortunately, an increase in gold particle size beyond 50 nm will prevent the desired induced color change upon aggregation. Further, the density of gold means that the bigger particles would not have the desired flow properties. Thus, while the inventors plan to continue to optimize gold particle based assays, they will also evaluate other types of improved particle materials such as silica or polystyrene of various sizes. The properties of the potential core particles are given in Table 2. Moving to either silica (Si) cores or polystyrene (PS) cores significantly reduces the density of the material and improves the settling velocity of the particles, resulting in an improved radial flow within the evaporating drop. Furthermore, there are a number of commercially available sources of Si and PS particles, providing a wide range of diameters and surface chemistries. The radial flow performance of the core particles will be determined. Particle performance will represent a balance between the radial flow to the pinning line and the rate of settling. In these experiments, equal concentrations of particles will be spotted on a uniform capture surface and the distribution of deposited material will be examined microscopically as a function of time.

Unlike Au nanoparticles, these new core particles will not undergo a color change upon aggregation. However, the inventors expect that the larger particle sizes coupled to the white color of the particles will result in a lower limit of detection and a higher visual contrast against a black background. This will be verified experimentally, in which serially diluted particles will be spotted in a 4 μl volume on a black-backed surface. The limit of detection will be examined both by microscopic examination using image analysis software and visual inspection.

Improved surface chemistry. With these new core particles, there will be a need to develop functionalization chemistries that will allow us to readily tune the particle surfaces to match the desired interfacial properties. Fortunately, the inventors have published a number of papers dealing with this problem. Using either carboxy- or amine-terminated Si or PS particles, the desired Ni(II)NTA capture ligand may be coupled to the particle with high efficiency (FIG. 21) using standard peptide synthesis approaches. Further, using the SMCC (Succinimidyl 4-[N-maleimidomethyl]cyclohexane-1-carboxylate) strategy, the inventors will be able to couple the synthesized thiol ligands (previously used for the Au particles) to the amine functionalized particles. These approaches will provide us the necessary flexibility to continue the use of modularly designed ligands, a method to vary the loading of capture agent on the particle, and a diverse chemistry to address potential problems.

Another critical objective is to maximize productive interactions between the aggregation particle and the malaria target while minimizing non-specific interactions. The inventors hypothesize that the observed loss of sensitivity seen for Au particles in Phase I may be due to non-specific metal complex interactions with serum proteins. Given the myriad of possible protein structures, it is easy to imagine how the surface of a protein could interact via weak coordination or electrostatic interactions with the aggregation particle. One approach to rectifying this problem is to investigate the metal dependence of these interactions. Charging the NTA ligand site with metals other than Ni(II) will allow us to investigate if there is any metal dependence in these non-specific interactions. In a preliminary experiment, we have charged M(II)NTA-polystyrene particles with M(II)=Co(II), Cu(II), Ni(II), and Zn(II) and performed an affinity pulldown experiment as described in the Phase I activities. The resulting SDS page gel of proteins eluted from the various particles (FIGS. 22A-B) reveals a possible metal dependence. When the same particles were examined for their ability to bind to a fluorescently labeled HRP II protein, all have a strong affinity for target, but there is a metal preference. This suggests that it may be possible to maximize productive interactions while minimizing non-specific ones as a function of divalent metal ion.

A second approach is to design a different capture ligand. While the original inspiration for the capture ligand was inspired by Ni(II)NTA chromatography of His-tagged proteins, the natural substrate for the HRP II target is Fe(III) protoporphyrin IX (heme). Using the same modular approach, a new capture ligand featuring a heme moiety has been synthesized (FIG. 23). This ligand can then be coupled to any of the particle surfaces. As with the M(II)NTA capture agents, the heme ligand will be evaluated for binding to substrate and non-specific interactions.

Selection of Capture Surface Format. Uniformly functionalized capture surfaces demonstrate low non-specific binding. However, due to the uniform density of capture agents along the surface, there is also a deposition of material, creating disks rather than the desired ring structures, resulting in a loss of contrast. Consequently, a strategy that minimizes interactions in the center of the drop, while maximizing the concentration of aggregated particles to the ring will increase sensitivity. To achieve such enhancement, the capture surfaces will be formatted with a center of non-interacting material (e.g., polyethylene glycol, PEG) that maintains excellent drop geometry and flow, with an outer ring of the capture surface. The inventors also have the capability to use a materials deposition printer (an inkjet printer for materials) to print small volumes of reactive PEG inks onto the capture surface. They have previously shown that the printing of reactive inks results in new functionalized surfaces. The advantage of the inkjet printer is that it is very rapid, allowing the prototyping of a wide variety of conditions to find the optimal surface formatting configuration.

EXAMPLE 4

Figure 24:
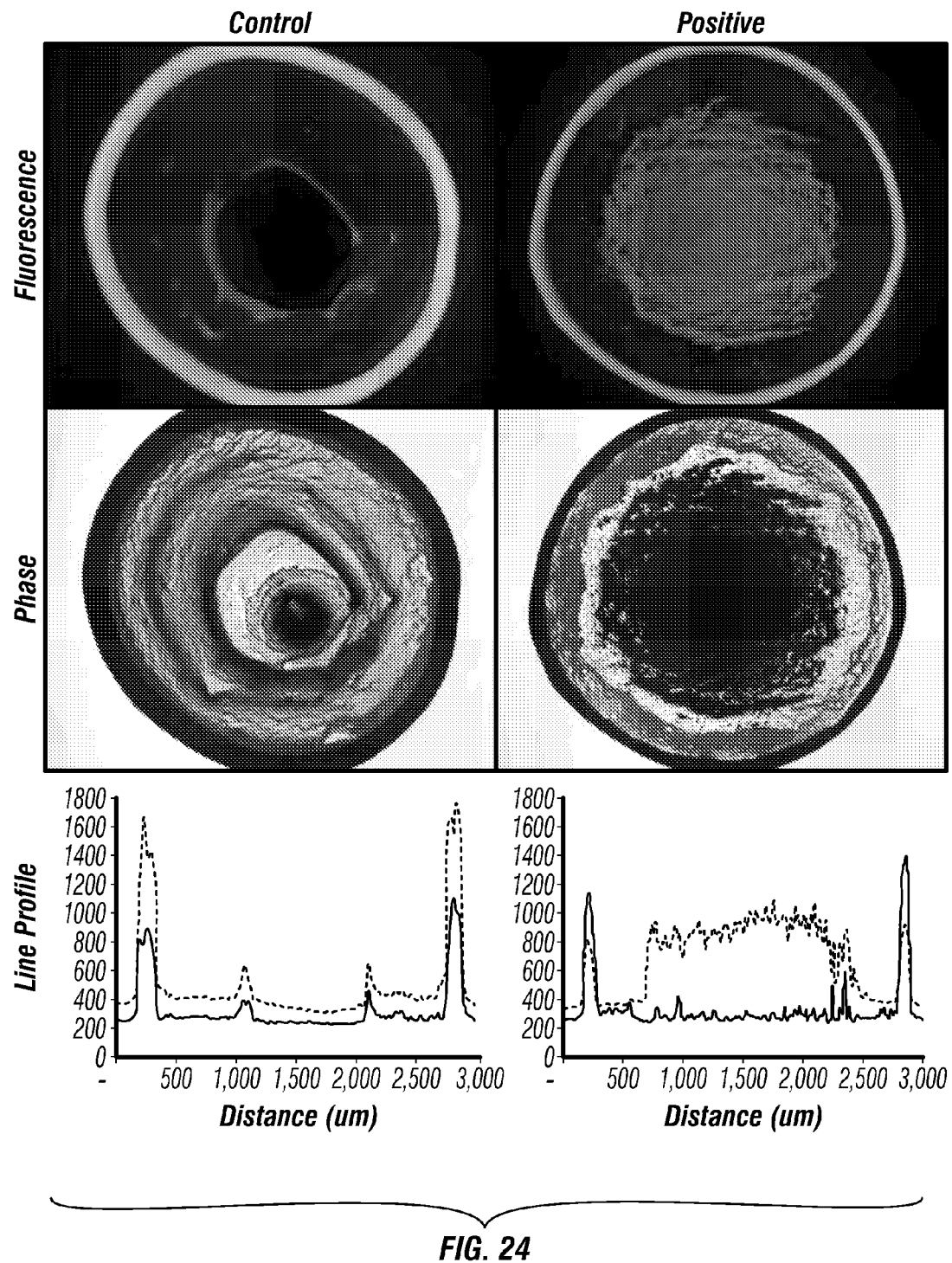
FIG. 24—Three-particle ring assay. An aqueous solution (15 mL) containing 435 nM poly-1-histidine (Sigma Aldrich, molecular weight=10 kDa) pH 4.5 was incubated at room temperature for 30 min with a 15 mL aqueous solution containing 1 mm diameter Ni(II)NTA polystyrene particles (Micromod Partikeltechnologie GmbH; $2 \times 10^7$ particles per mL). In the control sample, poly-1-histidine is replaced with poly-1-aspartic acid (Sigma Aldrich). Prior to incubation, the Ni(II)NTA polystyrene particles were surface-modified with fluorescein-labeled hexa-histidine tags (200,000 per particle). A 15 mL aqueous solution containing 250 nm diameter, dextran-stabilized Ni(II)NTA iron oxide particles (Micromod Partikeltechnologie GmbH; $4 \times 10^7$ particles per mL) was added to the reaction volume and incubated at room temperature for 30 min. A 15 mL aqueous solution containing 1 mm diameter, carboxylated polystyrene particles (Bangs Laboratories, Inc; $1.6 \times 10^7$ particles per mL) was then added to the reaction volume and incubated at room temperature for 10 min. Three-microliter drops of the positive and control samples were then deposited and dried on an unmodified glass slide and imaged with fluorescence microscopy.

FIG. 24 shows a three-particle ring assay. An aqueous solution (15 mL) containing 435 nM poly-1-histidine (Sigma Aldrich, molecular weight=10 kDa) pH 4.5 was incubated at room temperature for 30 min with a 15 mL aqueous solution containing 1 mm diameter Ni(II)NTA polystyrene particles (Micromod Partikeltechnologie GmbH; $2 \times 10^7$ particles per mL). In the control sample, poly-1-histidine is replaced with poly-1-aspartic acid (Sigma Aldrich). Prior to incubation, the Ni(II)NTA polystyrene particles were surface-modified with fluorescein-labeled hexa-histidine tags (200,000 per particle). A 15 mL aqueous solution containing 250 nm diameter, dextran-stabilized Ni(II)NTA iron oxide particles (Micromod Partikeltechnologie GmbH; $4 \times 10^7$ particles per mL) was added to the reaction volume and incubated at room temperature for 30 min. A 15 mL aqueous solution containing 1 mm diameter, carboxylated polystyrene particles (Bangs Laboratories, Inc; $1.6 \times 10^7$ particles per mL) was then added to the reaction volume and incubated at room temperature for 10 min. Three-microliter drops of the positive and control samples were then deposited and dried on an unmodified glass slide and imaged with fluorescence microscopy.

First, green polystyrene NiNTA particle was incubated with PLH (or control peptide). Poly-1-aspartic acid (PLAA) was used as the control peptide (molecular weight-matched). FeOx-NiNTA particle was added to the reaction volume, as was PS-cooh particle. All incubation times were 30 min each at room temperature. Final concentrations in the reaction volume are:

[PS-NiNTA]=5.106 per µL
[FeOx-NiNTA]=1.107 per µL
[PS-cooh]=4.106 per µL
[PLH or PLAA]=435 nM A 3 µL drop of the reacted solution was deposited on a standard glass slide centered above a magnet and evaporate until dry. The slides were imaged using fluorescence and phase microscopy and analyzed with Image Pro Plus software (v. 5.0).

The positive sample exhibits a red/orange ring color, whereas the control has a yellow/green ring color. A visibly detectable amount of green fluorescence is shifted to the center of the positive sample versus minimal settlement in the center of the control. The positive sample has a narrower ring structure than the control due to particles shifted to the center. The phase images show a significant increase in particles settled in the center of the positive and larger ring structure present in the positive sample. Line profiles taken across the equator of each image demonstrate the shift in green fluorescence distribution and the color components of the ring.

* * *

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. References

The following references, to the extent that they provide exemplary procedural or other details supplementary to those set forth herein, are specifically incorporated herein by reference.

Akompong et al., *J Biol Chem*, 277, 28923-33, 2002.
Axelrod, *Biophys. J.*, 26:557-573, 1979.
Baker et al., *J Infect Dis*, 192, 870-7, 2005.
Barton et al., ICONN, 2006.
Blackman et al., *Biophys. J.*, 71:194-208, 1996.
Brinas et al., *J Am Chem Soc*, 130, 975-982, 2008.
Cooke et al., *Trans R Soc Trop Med Hyg*, 86, 378, 1992.
Chiodini et al., *Trans R Soc Trop Med Hyg*, 101, 331-7, 2007.
De et al., *Macromol Biosci*, 9, 174-8, 2009.
Deegan et al., *Nature*, 389, 827-829, 1997.
Fatenejad, *J. Immunol.*, 152:5523-5531, 1994.
Gay et al., *Trans R Soc Trop Med Hyg*, 90, 516-8, 1996.
Ghimire et al., *Southeast Asian J Trop Med Public Health*, 34, 739-43, 2003.
Gupta et al., *Bioconjugate Chemistry*, 19, 1964-1967, 2008.
Hainfeld et al., *J Struct Biol*, 127, 185-198, 1999.
Hoet et al., *J. Immunol.*, 163:3304-3312, 1999.
Hoy et al., *Advanced Functional Materials*, 20:2240-2247, 2010.
Kifude et al., *Clin Vaccine Immunol*, 15, 1012-8, 2008.
Lauer et al., *Cytometry*, 48, 136-45, 2002.
Lee et al., *Langmuir*, 25, 657-660, 2009.
Lotz et al., *Mol. Biol. Rep.*, 16:127, 1992.
Love et al., *Chemical Reviews*, 105, 1103-1169, 2005.
Magnusson et al., *Scand. J. Immunol.*, 54:543-550, 2001.
Malmegrim et al., *Isr. Med. Assoc. J.*, 4:706-712, 2002.
Martin et al., *Am J Trop Med Hyg*, 80, 516-22, 2009.
Mrksich et al., *PNAS USA*, 93, 10775-10778, 1996.
Mohan et al., *J. Exp. Med.*, 177:1367-1381, 1993.
Moody, A., *Clin Microbiol Rev*, 15, 66-78, 2002.

Newkirk et al., *Arthritis Res.* 3:253-258, 2001.
Nyfors et al., *Biomacromolecules*, 10:1276-1281, 2009.
Ochola et al., *Lancet Infect Dis*, 6, 582-8, 2006.
Ogbonna & Uneke, *Trans R Soc Trop Med Hyg*, 102, 621-7, 2008.
Palegrosdemange et al., *J Am Chem Soc*, 113, 12-20, 1991.
Panton et al., *Mol Biochem Parasitol*, 35, 149-60, 1989.
Prime & Whitesides, *Science*, 252, 1164-1167, 1991.
Quintana et al., *S. Am J Trop Med Hyg*, 59, 868-71, 1998.
Rocheleau et al., *Biophys. J.*, 84(6):4078-4086, 2003.
Schmitt et al., *Biophys J*, 78, 3275-85, 2000.
Sharma et al., *J Clin Microbiol*, 46, 3759-65, 2008.
Sigal et al., *Analytical Chemistry*, 68, 490-497, 1996.
Singh et al., *Trop Med Int Health*, 5, 765-70, 2000.
Snounou et al., *Mol Biochem Parasitol*, 58, 283-92, 1993.
Srinivasan et al., *Ann Trop Med Parasitol*, 94, 227-32, 2000.
Tachibana et al., *Anal Biochem*, 359, 72-8, 2006.
Tinazli et al., *Chemistry—a European Journal*, 11, 5249-5259, 2005.
Vallin et al., *J. Immunol.*, 163:6306-6313, 1999.
ven Venrooij, *J. Clin. Invest.*, 86:2154-2160, 1990.
Warhurst & Williams, *J Clin Pathol*, 49, 533-8, 1996.
Weissbuch & Leiserowitz, *Chem Rev*, 108, 4899-914, 2008.
WHO Special Programme for Research & Training in Tropical Diseases, 2006.
WHO Malaria Fact Sheet, 2007.
WHO World Malaria Report, 2008.
Wilson et al., *Am J Trop Med Hyg*, 78, 733-735, 2008.
world-wide-web at gatesfoundation.org/topics/Pages/malaria.aspx

---

What is claimed is:

1. A method for detecting an analyte in a sample comprising:
   (a) providing a sample in a liquid form;
   (b) contacting said liquid sample with a capture particle that binds said analyte;
   (c) placing a drop of said liquid sample in step (b) on a non-permeable surface;
   (d) incubating said surface under conditions promoting evaporation of said drop, and
   (e) determining the presence or absence of said capture particle at said droplet edge
   wherein the presence of said capture particle at said droplet edge detects said analyte in said sample.

2. The method of claim 1, wherein said capture particle comprises (i) is a latex bead, a polystyrene bead, semiconductor bead/quantum dot, a metal particle, a paramagnetic particle, or a superparamagnetic particle; and (ii) an analyte binding agent.

3. The method of claim 2, wherein said capture particle is 1 nm to 100 μm in diameter.

4. The method of claim 2, wherein said capture particle is 1.001 gm/cm$^3$ to 20 gm/cm$^3$.

5. The method of claim 1, wherein said analyte binding agent is a protein, a chemical, a nucleic acid, a metal, or a carbohydrate.

6. The method of claim 5, wherein said protein is an antibody.

7. The method of claim 1, wherein said non-permeable surface is a glass, plastic or metal coated slide, a glass, plastic or metal rod, a glass, plastic or metal capillary tube, or a microarray pen.

8. The method of claim 1, wherein said analyte is a protein, a nucleic acid, a toxin, a lipid, a carbohydrate, a drug or chemical, or a metal.

9. The method of claim 1, wherein said liquid comprises a solvent selected from water, acetone, methanol, toluene, and ethanol.

10. The method of claim 1, wherein said sample is a foodstuff, water, soil, plant material, a biopsy, bronchial lavage, nasal lavage, nasal swab, cheek swab, or a body fluid.

11. The method of claim 1, further comprising washing said flat, non-permeable surface after step (d).

12. The method of claim 1, further comprising adding a detection agent that detects said capture particle bound to said analyte at said droplet edge.

13. The method of claim 1, wherein said capture particle exhibits a detectable change when aggregated.

14. The method of claim 1, wherein said capture particle is labeled.

15. The method of claim 1, wherein said non-permeable surface is derivatized to bind said capture particle.

16. The method of claim 1, wherein said non-permeable surface is derivatized to bind said analyte or to affect contact angle of a fluid.

17. The method of claim 1, wherein said capture particle is located on said non-permeable surface, and steps (b) and (c) are comprised in a single step of dropping said sample onto said non-permeable surface.

18. The method of claim 1, wherein steps (b) and (c) are reversed in order.

19. The method of claim 1, further comprising use of a precipitating particle that binds to said analyte and prevents movement of said capture particle to said edge of said drop.

20. The method of claim 1, further comprising using a detection particle that forms an aggregate with said capture particle in the presence of said analyte, and a detectable energy transfer reaction between said capture and detection particle occurs in said aggregate.

21. The method of claim 1, wherein detection comprises visual detection with the naked eye.

22. The method of claim 1, wherein detection comprises visual detection with a microscope.

23. The method of claim 1, wherein detection comprises automated detection of a light, a fluorescent, a color or a radioactive signal associated with said capture particle.

24. The method of claim 1, wherein said drop forms a spot of between 0.05 μm and 5000 μm.

25. The method of claim 1, wherein said drop, wherein said drop volume is between 0.1 μl to 100 μl.

26. The method of claim 1, wherein said capture particle further comprises an agent that reduces non-specific binding to other reagents.

27. A method for detecting an analyte in a sample comprising:
   (a) providing a sample in a liquid form;
   (b) contacting said liquid sample with (i) a capture particle that binds said analyte, wherein said capture particle is labeled with a first color, (ii) a control reaction particle labeled with a second color, and (iii) a precipitating particle that binds said analyte;
   (c) placing a drop of said liquid sample in step (b) on a non-permeable surface;
   (d) incubating said surface under conditions promoting evaporation of said drop; and
   (e) detecting said second color at said droplet edge when said analyte is present, or detecting a combination of said first and second colors at said droplet edge when said analyte is not present.

28. A method for detecting an analyte in a sample comprising:
- (a) providing a sample in a liquid form;
- (b) contacting said liquid sample with a capture particle that binds said analyte, wherein said capture particle is detectable when aggregated;
- (c) placing a drop of said liquid sample in step (b) on a non-permeable surface, wherein said surface is derivatized to bind said analyte;
- (d) incubating said surface under conditions promoting evaporation of said drop;
- (e) washing said surface; and
- (f) detecting said aggregate at said droplet edge when said analyte is present, or not detecting an aggregate at said droplet edge when said analyte is not present.

* * * * *

SEQUENCE LISTING

```
<160> NUMBER OF SEQ ID NOS: 1

<210> SEQ ID NO 1
<211> LENGTH: 326
<212> TYPE: PRT
<213> ORGANISM: Artificial Sequence
<220> FEATURE:
<223> OTHER INFORMATION: Synthetic peptide

<400> SEQUENCE: 1

Met Val Ser Phe Ser Lys Asn Lys Val Leu Ser Ala Ala Val Phe Ala
1               5                   10                  15

Ser Val Leu Leu Leu Asp Asn Asn Ser Ala Phe Asn Asn Asn Leu
            20                  25                  30

Cys Ser Lys Asn Ala Lys Gly Leu Asn Leu Asn Lys Arg Leu Leu His
        35                  40                  45

Glu Thr Gln Ala His Val Asp Asp Ala His His Ala His His Val Ala
    50                  55                  60

Asp Ala His His Ala His His Ala His His Ala Ala Asp Ala His His
65                  70                  75                  80

Ala His His Ala Ala Asp Ala His His Ala His His Ala Ala Asp Ala
                85                  90                  95

His His Ala His His Ala Ala Asp Ala His His Ala His His Ala Ala
            100                 105                 110

Asp Ala His His Ala His His Ala Ala Asp Ala His His Ala His His
        115                 120                 125

Met Asp Ala His His Ala His His Met Asp Ala His His Ala His His
    130                 135                 140

Ala Ala Asp Ala His His Ala His His Met Tyr Ala His His Ala His
145                 150                 155                 160

His Ala Ser Asp Ala His His Ala Ala Asp Ala His His Ala Ala Tyr
                165                 170                 175

Ala His His Ala His His Ala Ala Asp Ala His His Ala Ala Asp Ala
            180                 185                 190

His His Met Tyr Ala His His Ala His His Met Asp Ala His His Ala
        195                 200                 205

Ala Asp Ala His His Ala Thr Asp Ala His His Ala His His Ala Ala
    210                 215                 220

Asp Ala His His Ala Thr Asp Ala His His Ala Ala Asp Ala His His
225                 230                 235                 240

Met Asp Ala His His Ala Thr Asp Ala His His Ala Ala Asp Ala His
                245                 250                 255
```

```
His Ala Ile Asp Ala His His Ala Ala Asp Ala His His Ala Ala Asp
                260             265             270

Ala His His Ala Thr Asp Ser His Ala His His Ala Ala Asp Ala
        275             280             285

His His Ala Ala Ala His His Ala Thr Asp Ala His His Ala Ala Ala
        290             295             300

His His Ala Thr Asp Ala His His Ala Ala Ala His His Glu Ala Ala
305             310             315             320

Thr His Cys Leu Arg His
                325
```